US011155802B2

(12) United States Patent
Frevert et al.

(10) Patent No.: US 11,155,802 B2
(45) Date of Patent: Oct. 26, 2021

(54) RECOMBINANT BOTULINUM NEUROTOXINS WITH INCREASED DURATION OF EFFECT

(71) Applicant: MERZ PHARMA GMBH & CO. KGAA, Frankfurt am Main (DE)

(72) Inventors: Jürgen Frevert, Berlin (DE); Fred Hofmann, Potsdam (DE); Marcel Jurk, Berlin (DE); Manuela López De La Paz, Liederbach am Taunus (DE); Daniel Scheps, Potsdam (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 16/498,257

(22) PCT Filed: Jul. 6, 2017

(86) PCT No.: PCT/EP2017/066891
§ 371 (c)(1),
(2) Date: Sep. 26, 2019

(87) PCT Pub. No.: WO2019/007509
PCT Pub. Date: Jan. 10, 2019

(65) Prior Publication Data
US 2020/0131494 A1    Apr. 30, 2020

(51) Int. Cl.
*C12N 9/52*    (2006.01)

(52) U.S. Cl.
CPC ........ *C12N 9/52* (2013.01); *C12Y 304/24069* (2013.01)

(58) Field of Classification Search
None
See application file for complete search history.

(56) References Cited

U.S. PATENT DOCUMENTS

| 6,903,187 | B1 | 6/2005 | Steward et al. |
| 7,491,799 | B2 | 2/2009 | Steward et al. |
| 8,444,991 | B2 | 5/2013 | Randolph et al. |
| 8,563,521 | B2 | 10/2013 | Skerra et al. |
| 8,748,151 | B2 | 6/2014 | Frevert |
| 8,808,710 | B2 | 8/2014 | Randolph et al. |
| 9,050,246 | B2 | 6/2015 | Bertholon et al. |
| 9,050,336 | B2 | 6/2015 | Blanda et al. |
| 9,161,970 | B2 | 10/2015 | Tezel et al. |
| 9,260,494 | B2 | 2/2016 | Skerra et al. |
| 9,388,394 | B2 | 7/2016 | Heinrichs et al. |
| 9,758,573 | B2 | 9/2017 | Vartanian et al. |
| 9,809,809 | B2 * | 11/2017 | Schmidt .................. A61P 19/00 |
| 9,827,298 | B2 | 11/2017 | Hofmann et al. |
| 9,975,929 | B2 | 5/2018 | Frevert et al. |
| 10,022,424 | B2 | 7/2018 | Stossel et al. |
| 10,603,353 | B2 * | 3/2020 | Frevert .................. C12N 15/70 |
| 2002/0127247 | A1 | 9/2002 | Steward et al. |
| 2010/0172940 | A1 | 7/2010 | Petrella |
| 2012/0135937 | A1 | 5/2012 | Bertholon et al. |
| 2012/0141532 | A1 | 6/2012 | Blanda et al. |
| 2012/0295914 | A1 | 11/2012 | Villard et al. |
| 2013/0165389 | A1 | 6/2013 | Schellenberger et al. |
| 2014/0308267 | A1 * | 10/2014 | Schmidt .................. A61P 17/10 424/94.67 |
| 2015/0044250 | A1 | 2/2015 | Heinrichs et al. |
| 2015/0320743 | A1 | 11/2015 | Bertholon et al. |
| 2015/0322118 | A1 | 11/2015 | Groer et al. |
| 2017/0058006 | A1 | 3/2017 | Frevert et al. |
| 2018/0141982 | A1 | 5/2018 | Anderson et al. |
| 2018/0169182 | A1 * | 6/2018 | Frevert ................ A61K 38/164 |
| 2018/0327730 | A1 * | 11/2018 | Hofmann ................ C12N 9/52 |
| 2019/0060422 | A1 | 2/2019 | Fink et al. |
| 2020/0048624 | A1 * | 2/2020 | Hofmann ................ A61K 8/64 |
| 2020/0129587 | A1 * | 4/2020 | Frevert .................. C12N 15/70 |
| 2020/0131494 | A1 * | 4/2020 | Frevert .................. C07K 14/33 |
| 2020/0354706 | A1 | 11/2020 | Frevert et al. |
| 2021/0008156 | A1 | 1/2021 | Frevert et al. |

FOREIGN PATENT DOCUMENTS

| EP | 2369005 | | 9/2011 | |
| EP | 3335719 | A1 * | 6/2018 | ...... C12Y 304/24069 |
| EP | 3649143 | A1 * | 5/2020 | ............. C12N 9/52 |
| RU | 2530604 | | 7/2013 | |
| WO | WO 1995/032738 | | 12/1995 | |
| WO | WO 1996/039166 | | 12/1996 | |
| WO | WO 2000/012728 | | 3/2000 | |
| WO | WO 2001/014570 | | 3/2001 | |
| WO | WO 2002/008268 | | 1/2002 | |
| WO | WO 2002/040506 | | 5/2002 | |
| WO | WO 2005/007185 | | 1/2005 | |
| WO | WO 2005/068494 | | 7/2005 | |
| WO | WO 2006/017749 | | 2/2006 | |
| WO | WO 2006/020208 | | 2/2006 | |
| WO | WO 2006/076902 | | 7/2006 | |

(Continued)

OTHER PUBLICATIONS

Binz et al, Abstracts/Toxicon 156 (2018):S10 Abstract #20 (Year: 2018).*
Fan et al, PLoS One, PLoS ONE 10(8): e0135306. doi:10.1371/journal.pone.0135306. Published Aug. 14, 2015 (Year: 2015).*

(Continued)

*Primary Examiner* — Nita M. Minnifield
(74) *Attorney, Agent, or Firm* — Leydig, Voit & Mayer, Ltd.

(57) ABSTRACT

This invention relates to novel recombinant botulinum neurotoxins serotype A exhibiting both (i) an increased duration of effect and (ii) a high specific biological activity. These novel recombinant botulinum neurotoxins comprise at least two additional domains consisting of proline, alanine and an additional amino acid residue and at least one amino acid modification which is located at the alpha-exosite or at the beta-exosite of the light chain of the neurotoxin. The invention further relates to novel recombinant single-chain precursor botulinum neurotoxins and compositions comprising the recombinant botulinum neurotoxin with an increased duration of effect and a high specific biological activity.

13 Claims, 5 Drawing Sheets

Figure 1:
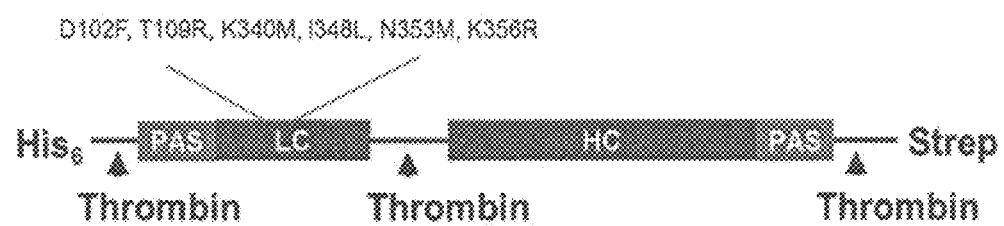

Specification includes a Sequence Listing.

(56) References Cited

FOREIGN PATENT DOCUMENTS

| WO | WO 2008/155134 | | 12/2008 | | |
|----|----|----|----|----|----|
| WO | WO 2009/114748 | | 9/2009 | | |
| WO | WO 2010/028025 | | 3/2010 | | |
| WO | WO 2010/091122 | | 8/2010 | | |
| WO | WO 2010/136585 | | 12/2010 | | |
| WO | WO 2010/136594 | | 12/2010 | | |
| WO | WO 2011/109130 | | 9/2011 | | |
| WO | WO 2011/123813 | | 10/2011 | | |
| WO | WO 2011/144756 | | 11/2011 | | |
| WO | WO 2012/052562 | | 4/2012 | | |
| WO | WO 2013/049508 | | 4/2013 | | |
| WO | WO 2013/068472 | | 5/2013 | | |
| WO | WO-2013068476 | A1 * | 5/2013 | ............. | A61P 15/02 |
| WO | WO 2013/082116 | | 6/2013 | | |
| WO | WO 2013/112867 | | 8/2013 | | |
| WO | WO 2014/068317 | | 5/2014 | | |
| WO | WO 2014/086494 | | 6/2014 | | |
| WO | WO 2014/207109 | | 12/2014 | | |
| WO | WO 2015/132004 | | 9/2015 | | |
| WO | WO 2015/183044 | | 12/2015 | | |
| WO | WO 2016/025626 | | 2/2016 | | |
| WO | WO 2016/073562 | | 5/2016 | | |
| WO | WO 2016/110662 | | 7/2016 | | |
| WO | WO-2016180533 | A1 * | 11/2016 | ............. | C07K 14/33 |
| WO | WO 2016/198163 | | 12/2016 | | |
| WO | WO 2017/125487 | | 7/2017 | | |
| WO | WO 2018/233813 | | 12/2018 | | |
| WO | WO 2019/007509 | | 1/2019 | | |
| WO | WO-2019007509 | A1 * | 1/2019 | ............. | C12N 9/52 |
| WO | WO-2019081022 | A1 * | 5/2019 | ............. | C07K 14/33 |
| WO | WO-2019101308 | A1 * | 5/2019 | ............. | A61K 8/99 |
| WO | WO-2020088667 | A1 * | 5/2020 | ............. | C12N 15/00 |

OTHER PUBLICATIONS

Kumaran et al, PLoS Pathogens 4(9): e1000165. doi:10.1371/journal.ppat.1000165. Published: Sep. 26, 2008 (Year: 2008).*
Shao et al, BBA-General Subjects, 1863 (2019)129396. Available online:Jul. 11, 2019 (Year: 2019).*
Wang et al. Biochimica et Biophysica Acta. 1834 (2013) 2722-2728. Available online: Oct. 2, 2013 (Year: 2013).*
Arndt et al., Journal Molecular Biology, 2006, 362:733-742 (Year: 2006).*
Stancombe et al. FEBS Journal, 2012, 279:515-523 (Year: 2012).*
Aoki (2001) "A comparison of the safety margins of botulinum neurotoxin serotypes A, B, and F in mice," Toxicon 39: 1815-1820.
Arndt et al. (2006) "A Structural Perspective of the Sequence Variability Within Botulinum Neurotoxin Subtypes A1-A4," Journal of Molecular Biology 362(4): 733-742.
Cox (2008) "Botox Jabs: A New Weapon Against Chronic Pain," ABC News, available online at https://abcnews.go.com/Health/PainManagement/story?id=4148566&page=1, 2 pp.
Fernandez-Salas et al. (2004) "Plasma membrane localization signals in the light chain of botulinum neurotoxin," Proc. Natl. Acad. Sci. U.S.A. 101(9): 3208-3213.
Li et al. (1998) "Molecular characterization of type E Clostridium botulinum and comparison to other types of Clostridium botulinum," Biochim. Biophys. Acta. 1395(1):21-27.
Schlapschy et al. (2013) "PASylation: a biological alternative to PEGylation for extending the plasma half-life of pharmaceutically active proteins," Protein Engineering, Design and Selection 26(8): 489-501.
Search Report dated May 6, 2015, corresponding to International Application No. PCT/EP2015/000489 (filed Mar. 4, 2015), 4 pp.
Search Report and Written Opinion, dated Sep. 26, 2016, corresponding to International Application No. PCT/EP2016/000962 (filed Jun. 10, 2016), 10 pp.
Search Report and Written Opinion, dated Dec. 1, 2017, corresponding to International Application No. PCT/EP2017/066891 (filed Jul. 6, 2017), 12 pp.

Stancombe et al. (Feb. 2012) "Engineering botulinum neurotoxin domains for activation by toxin light chain," Febs Journal 279(3): 515-523.
Wang et al. (2011) "A Dileucine in the Protease of Botulinum Toxin A Underlies Its Long-lived Neuroparalysis," J. Biol. Chem. 286(8): 6375-6385.
Xue et al. (Nov. 2014) "Probing BoNT/A Protease Exosites: Implications for Inhibitor Design and Light Chain Longevity," Biochemistry 53(43): 6820-6824.
Altschul et al. (1990) "Basic local alignment search tool," J. Mol. Bio. 215(3): 403-410.
Band et al. (2010) "Recombinant derivatives of botulinum neurotoxin A engineered for trafficking studies and neuronal delivery," Protein Expression and Purification, Academic Press 71(1): 62-73.
"BPXTEN construction related XTEN polypeptide sequence SEQ ID 767," XP002776714, retrieved from EBI accession No. GSP: AYG93920, Database accession No. AYG93920 Sep. 2010, 2 pp.
Breidenbach et al. (2004) "Substrate recognition strategy for botulinum neurotoxin serotype A," Nature 432: 925-929.
Dressler et al. (2005) "Mouse diaphragm assay for detection of antibodies against botulinum toxin type B," Movement Disorders 20(12): 1617-1619.
Hallis et al. (1996) "Development of novel assays for botulinum type A and B neurotoxins based on their endopeptidase activities," J. Clin. Microbiol. 34(8): 1934-1938.
Higgins et al. (1989) "Fast and sensitive multiple sequence alignments on a microcomputer," CABIOS 5(2): 151-153.
International Preliminary Report on Patentability, dated Jan. 2, 2020, corresponding to International Application No. PCT/EP2017/065096 (filed Jun. 20, 2017), 7 pp.
International Preliminary Report on Patentability, dated Jan. 16, 2020, corresponding to International Application No. PCT/EP2017/066891 (filed Jul. 6, 2017), 9 pp.
International Preliminary Report on Patentability, dated May 7, 2020, corresponding to International Application No. PCT/EP2017/077427 (filed Oct. 28, 2017), 8 pp.
International Preliminary Report on Patentability, dated Jun. 4, 2020, corresponding to International Application No. PCT/EP2017/080117 (filed Nov. 22, 2017), 11 pp.
Jones et al. (2008) "Development of improved SNAP25 endopeptidase immunoassays for botulinum type A and E toxins," J. of Immunological Methods 329(1-2): 92-101.
KELLER (2006) "Recovery from botulinum neurotoxin poisoning in vivo," Neuroscience 139(2): 629-637.
Needleman et al. (1970) "A general method applicable to the search for similarities in the amino acid sequence of two proteins," J Mol Biol 48: 443-453.
Pearce et al. (1994) "Measurement of Botulinum Toxin Activity: Evaluation of the Lethality Assay," Toxicol. Appl. Pharmacol. 128(1): 69-77.
Ravichandran et al. (2006) "An Initial Assessment of the Systemic Pharmacokinetics of Botulinum Toxin," JPET 318(3):1343-1351.
Search Report and Written Opinion, dated Jan. 8, 2018, corresponding to International Application No. PCT/EP2017/065096 (filed Jun. 20, 2017), 10 pp.
Search Report and Written Opinion, dated Feb. 20, 2018, corresponding to International Application No. PCT/EP2017/077427 (filed Oct. 26, 2017), 11 pp.
Search Report and Written Opinion, dated Jun. 18, 2018, corresponding to International Application No. PCT/EP2017/080117 (filed Nov. 22, 2017), 18 pp.
Smith et al. (1981) "Comparison of biosequences," Adv Appl Math 2: 482-489.
Vazquez-Cintron et al. (Aug. 2016) "Pre-Clinical Study of a Novel Recombinant Botulinum Neurotoxin Derivative Engineered for Improved Safety," Scientific Reports 6(1), 30429: 1-10.
Weber (2013) "Inhibierung von Stat5 in Tumoren durch RNA-Interferenz und spezifische Interaktion eines Peptidaptamer-Konstruktes milder DNA-Bindedomane," PhD thesis, Johann-Wolfgang-Goethe Universitat, Frankfurt am Main (Germany).
"Botulinum neurotoxin type E non-toxic component," (1993) available online at https://www.ncbi.nlm.nih.gov/protein/p46082, accessed Dec. 2017.

(56) References Cited

OTHER PUBLICATIONS

European Search Report, dated Aug. 29, 2016, corresponding to European Patent Application No. 16 15 8302.6, 5 pp.
Ganceviciene et al. (2012) "Skin anti-aging strategies," Dermato-endocrinology 4(3): 308-319.
International Search Report and Written Opinion in corresponding International Patent Application No. PCT/EP2017/054596, dated May 23, 2017, 9 pp.
International Preliminary Report on Patentability in corresponding International Patent Application No. PCT/EP2017/054596, dated Sep. 4, 2018, 7 pp.
Kolbin et al. (2014) "Pharmacoepidemiology of botulinum toxin preparations in comprehensive post-stroke spasticity therapy in the Russian Federation: Survey data from neurologists" Kachestvennaya Klinicheskaya Praktika 3: 13 pages.
Kukreja et al. (2015) "The botulinum toxin as a therapeutic agent: molecular and pharmacological insights," Research and Reports in Biochemistry 5:173-183.
Owen et al. (2017) "Hyaluronic Acid," Comprehensive Biomaterials II, Chapter 2.14 2: 306-331, Abstract Only (3 pages).
Pearson et al. (1988) "Improved tools for biological sequence comparison," PNAS 85(8): 2444-2448.
Tosoh Application Note (2020) "Analysis of Hyaluronic Acid Using the EcoSEC® GPC System," Available online at https://www.ecosec.eu//SharedTBGFilelibrary/TBG/Products%20Download/Application%20Note/a17i17a.pdf, pp. 1-3.
USPTO Office Action, dated Mar. 2, 2021, corresponding to U.S. Appl. No. 16/079,367,11 pp.
U.S. Appl. No. 16/079,367, filed Aug. 23, 2018.

\* cited by examiner

RECOMBINANT BOTULINUM NEUROTOXINS WITH INCREASED DURATION OF EFFECT

CROSS-REFERENCE TO RELATED APPLICATIONS

This application is a U.S. National Stage Application filed under 35 U.S.C. § 371 of International Application No. PCT/EP2017/066891, filed Jul. 6, 2017, which is hereby incorporated by reference in its entirety.

FIELD OF THE INVENTION

This invention relates to novel recombinant botulinum neurotoxins serotype A exhibiting both (i) an increased duration of effect and (ii) a high specific biological activity. The invention also relates to methods for the manufacture of such recombinant botulinum neurotoxins. These novel recombinant botulinum neurotoxins comprise at least two additional domains and least one amino acid modification which is located at the alpha-exosite and/or at the beta-exosite of the light chain of the neurotoxin. The invention further relates to pharmaceutical compositions comprising said recombinant neurotoxins. The invention further relates to novel recombinant single-chain precursor botulinum neurotoxins and nucleic acid sequences encoding such recombinant single-chain precursor botulinum neurotoxins.

BACKGROUND OF THE INVENTION

*Clostridium* is a genus of anaerobe gram-positive bacteria, belonging to the Firmicutes. *Clostridium* consists of around 100 species that include common free-living bacteria as well as important pathogens, such as *Clostridium botulinum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterised by paralysis of various muscles. Paralysis of the breathing muscles can cause death of the affected individual.

Although both botulinum neurotoxin (BoNT) and tetanus neurotoxin (TxNT) function via a similar initial physiological mechanism of action, inhibiting neurotransmitter release from the axon of the affected neuron into the synapse, they differ in their clinical response. While the botulinum toxin acts at the neuromuscular junction and other cholinergic synapses in the peripheral nervous system, inhibiting the release of the neurotransmitter acetylcholine and thereby causing flaccid paralysis, the tetanus toxin acts mainly in the central nervous system, preventing the release of the inhibitory neurotransmitters GABA (gamma-aminobutyric acid) and glycine by degrading the protein synaptobrevin. The consequent overactivity in the muscles results in generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic types, termed BoNT/A through BoNT/G. Most *Clostridium botulinum* strains produce one type of neurotoxin, but strains producing multiple toxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial toxins, is located between the two cysteine residues forming the disulfide bond. This loop region is proteolytically cleaved by an unknown clostridial endoprotease to obtain the biologically active toxin.

The molecular mechanism of intoxication by TeNT and BoNT appears to be similar as well: entry into the target neuron is mediated by binding of the C-terminal part of the heavy chain to a specific cell surface receptor; the toxin is then taken up by receptor-mediated endocytosis. The low pH in the so formed endosome then triggers a conformational change in the clostridial toxin which allows it to embed itself in the endosomal membrane and to translocate through the endosomal membrane into the cytoplasm, where the disulfide bond joining the heavy and the light chain is reduced. The light chain can then selectively cleave so called SNARE-proteins, which are essential for different steps of neurotransmitter release into the synaptic cleft, e.g. recognition, docking and fusion of neurotransmitter-containing vesicles with the plasma membrane. TeNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C cleaves the integral plasma membrane protein syntaxin and SNAP-25.

Clostridial neurotoxins display variable durations of action that are serotype specific. The clinical therapeutic effect of BoNT/A lasts approximately 3 months for neuromuscular disorders and 6 to 12 months for hyperhidrosis. The effect of BoNT/E, on the other hand, lasts less than 4 weeks. The longer lasting therapeutic effect of BoNT/A makes it preferable for certain clinical use compared to the other serotypes, for example serotypes B, $C_1$, D, E, F, G. One possible explanation for the divergent durations of action might be the distinct subcellular localizations of BoNT serotypes. The protease domain of BoNT/A light chain localizes in a punctate manner to the plasma membrane of neuronal cells, co-localizing with its substrate SNAP-25. In contrast, the short-duration BoNT/E serotype is cytoplasmic. Membrane association might protect BoNT/A from cytosolic degradation mechanisms allowing for prolonged persistence of BoNT/A in the neuronal cell.

In *Clostridium botulinum*, the botulinum toxin is formed as a protein complex comprising the neurotoxic component and non-toxic proteins. The accessory proteins embed the neurotoxic component thereby protecting it from degradation by digestive enzymes in the gastrointestinal tract. Thus, botulinum neurotoxins of most serotypes are orally toxic. Complexes with, for example, 450 kDa or with 900 kDa are obtainable from cultures of *Clostridium botulinum*.

In recent years, botulinum neurotoxins have been used as therapeutic agents in the treatment of dystonias and spasms. Preparations comprising botulinum toxin complexes are commercially available, e.g. from Ipsen Ltd (Dysport®) or Allergan Inc. (Botox®). A high purity neurotoxic component, free of any complexing proteins, is for example available from Merz Pharmaceuticals GmbH, Frankfurt (Xeomin®).

Clostridial neurotoxins are usually injected into the affected muscle tissue, bringing the agent close to the neuromuscular end plate, i.e. close to the cellular receptor mediating its uptake into the nerve cell controlling said affected muscle. Various degrees of neurotoxin spread have been observed. The neurotoxin spread is thought to depend on the injected amount and the particular neurotoxin preparation. It can result in adverse side effects such as paralysis in nearby muscle tissue, which can largely be avoided by reducing the injected doses to the therapeutically relevant level. Overdosing can also trigger the immune system to generate neutralizing antibodies that inactivate the neurotoxin preventing it from relieving the involuntary muscle activity. Immunologic tolerance to botulinum toxin has been shown to correlate with cumulative doses.

At present, clostridial neurotoxins are still predominantly produced by fermentation processes using appropriate *Clostridium* strains. However, industrial production of clostridial neurotoxin from anaerobic *Clostridium* culture is a cumbersome and time-consuming process. Due to the high toxicity of the final product, the procedure must be performed under strict containment. During the fermentation process, the single-chain precursors are proteolytically cleaved by an unknown clostridial protease to obtain the biologically active di-chain clostridial neurotoxin. The degree of neurotoxin activation by proteolytic cleavage varies between different strains and neurotoxin serotypes, which is a major consideration for the manufacture due to the requirement of neurotoxin preparations with a well-defined biological activity. Furthermore, during fermentation processes using *Clostridium* strains the clostridial neurotoxins are produced as protein complexes, in which the neurotoxic component is embedded by accessory proteins. These accessory proteins have no beneficial effect on biological activity or duration of effect. They can however trigger an immune reaction in the patient, resulting in immunity against the clostridial neurotoxin. Manufacture of recombinant clostridial neurotoxins, which are not embedded by auxiliary proteins, might therefore be advantageous.

Methods for the recombinant expression of clostridial neurotoxins in *E. coli* are well known in the art (see, for example, WO 00/12728, WO 01/14570, or WO 2006/076902). Furthermore, clostridial neurotoxins have been expressed in eukaryotic expression systems, such as in *Pichia pastoris, Pichia methanolica, Saccharomyces cerevisiae*, insect cells and mammalian cells (see WO 2006/017749).

Recombinant botulinum neurotoxins may be expressed as single-chain precursors, which subsequently have to be proteolytically cleaved to obtain the final biologically active botulinum neurotoxin. Thus, botulinum neurotoxins may be expressed in high yield in rapidly-growing bacteria as relatively non-toxic single-chain polypeptides.

Furthermore, it might be advantageous to modify botulinum neurotoxin characteristics regarding biological activity, cell specificity, antigenic potential and duration of effect by genetic engineering to obtain recombinant neurotoxins with new therapeutic properties in specific clinical areas. Genetic modification of botulinum neurotoxins might allow altering the mode of action or expanding the range of therapeutic targets.

Botulinum toxin variants exhibiting an increased duration of effect and a high specific biological activity in neuromuscular tissue than naturally occurring botulinum toxins would be very advantageous in order to reduce administration frequency and the incidence of neutralizing antibody generation since immunologic tolerance to botulinum toxin is correlated with cumulative doses.

US 2002/0127247 describes clostridial neurotoxins comprising modifications in secondary modification sites and exhibiting altered biological persistence.

There is a strong demand to produce new botulinum neurotoxins serotype A with an increased duration of effect and with improved properties, in order to allow for exploitation of the therapeutic potential of BoNT serotype A, which have so far been considered impractical for certain clinical application. Ideally, the increased duration of effect of a particular botulinum neurotoxin serotype A could be adjusted in a tailor-made fashion in order to address any particular features and demands of a given indication, such as the amount of neurotoxin being administered, frequency of administration etc. In addition, it would be desirable to produce botulinum neurotoxins serotype A which exhibit an increased duration of effect than naturally occurring botulinum toxins serotype A with a high specific biological activity. To date, such aspects have not been solved satisfactorily.

OBJECTS OF THE INVENTION

It was an object of the invention to overcome the above illustrated drawbacks. In particular, it was an object of the invention to provide recombinant botulinum neurotoxins serotype A exhibiting an increased duration of effect than naturally occurring botulinum toxins with a high specific biological activity in neuromuscular tissue and to establish a reliable and accurate method for manufacturing and obtaining such recombinant botulinum neurotoxins. Such a method and novel precursor botulinum neurotoxins used in such methods would serve to satisfy the great need for recombinant botulinum neurotoxins exhibiting an increased duration of effect with a high specific biological activity.

SUMMARY OF THE INVENTION

The naturally occurring botulinum toxin serotypes display highly divergent durations of effect, probably due to their distinct subcellular localization. BoNT/A exhibits the longest persistence and was shown to localize in the vicinity of the plasma membrane of neuronal cells. However, additional factors such as degradation, spread or diffusion, and/or translocation rates might have a decisive impact on the differences in the duration for the individual botulinum toxin serotypes.

So far, except for the approach described and claimed in WO 2015/132004, no generally applicable method for modifying clostridial neurotoxins to increase their duration of effect is available. According to WO 2015/132004, a recombinant botulinum neurotoxin comprising a domain consisting of proline (P), alanine (A) and serine (S) residues (hereafter referred to "PASylated" botulinum neurotoxins) exhibits an increased duration of effect compared to a corresponding wildtype botulinum neurotoxin, but it was shown that such a "PASylated" botulinum neurotoxin also exhibits a decreased specific potency, i.e. a decreased specific biological activity compared to a corresponding wildtype botulinum neurotoxin. This means for the clinical setting, that a higher amount of such a modified botulinum neurotoxin has to be injected into a subject/patient to reach the same paralytic effect in comparison to a wildtype botulinum neurotoxin which in turn increases the risk of generating neutralizing antibodies that inactivate the neurotoxin.

Surprisingly, it has been found that recombinant botulinum neurotoxins serotype A having an increased duration of effect compared to a corresponding wildtype botulinum neurotoxin and a high specific potency, i.e. a high specific biological activity can be obtained by a two-fold modification. On the one hand these neurotoxins comprise at least two additional domains consisting of proline, alanine and an additional amino acid residue. Secondly, these neurotoxins according to the invention comprise at least one amino acid modification which is located at the alpha-exosite and/or at the beta-exosite of the light chain of the neurotoxin.

Thus, in one aspect, the present invention relates to a recombinant botulinum neurotoxin serotype A comprising at least two domains wherein each domain comprises an amino acid sequence consisting of at least 50 amino acid residues, wherein said amino acid sequence consists of at least one proline, at least one alanine and at least one additional amino acid residue, selected from the group consisting of serine, threonine, tyrosine and glutamine, wherein the neurotoxin further comprises at least one amino acid modification which is located at the alpha-exosite and/or at the beta-exosite of the light chain of the neurotoxin.

In another aspect, the present invention relates to a composition, in particular to a pharmaceutical composition comprising the recombinant botulinum neurotoxin of the present invention.

In yet another aspect, the present invention relates to the use of the composition of the present invention for cosmetic treatment.

In another aspect, the present invention relates to a method for the generation of the recombinant botulinum neurotoxin of the present invention, comprising the step of obtaining a recombinant nucleic acid sequence encoding a recombinant single-chain precursor botulinum neurotoxin serotype A by modifying the nucleic acid sequence of the botulinum neurotoxin serotype A accordingly.

In another aspect, the present invention relates to a recombinant single-chain precursor botulinum neurotoxin serotype A comprising at least two additional domains wherein each domain comprises an amino acid sequence consisting of at least 50 amino acid residues, wherein said amino acid sequence consists of at least one proline, at least one alanine and at least one additional amino acid residue, selected from the group consisting of serine, threonine, tyrosine and glutamine, and a modified alpha-exosite and/or beta-exosite of the light chain.

In another aspect, the present invention relates to a nucleic acid sequence encoding the recombinant single-chain precursor botulinum neurotoxin serotype A of the present invention.

In another aspect, the present invention relates to a method for obtaining the nucleic acid sequence of the present invention, comprising the step of adding nucleic acid sequences to the heavy and the light chain and in addition modifying a nucleic acid sequence encoding the alpha-exosite and/or at the beta-exosite of the light chain of the parental botulinum neurotoxin serotype A.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor botulinum neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

FIGURES

FIG. 1: Schematic Presentation of a modified botulinum toxin A (MaJ007=PAS100-BoNT/A (D102F T109R K340M I348L N353M K356R)-PAS100=PAS100-BoNT/A-ISA2-PAS100), wherein both the light chain (LC) and the heavy chain (HC) each comprise an additional amino acid sequence consisting of 100 amino acid residues, wherein said amino acid sequence consists of proline (P), alanine (A) and serine (S) residues (PAS) and wherein the light chain (LC) comprises six amino acid modifications which are located at the alpha-exosite at positions D102, T109, K340, I348, N353, K356, wherein these amino acids are substituted as follows D102F, T109R, K340M, I348L, N353M, K356R.

Figure 2:
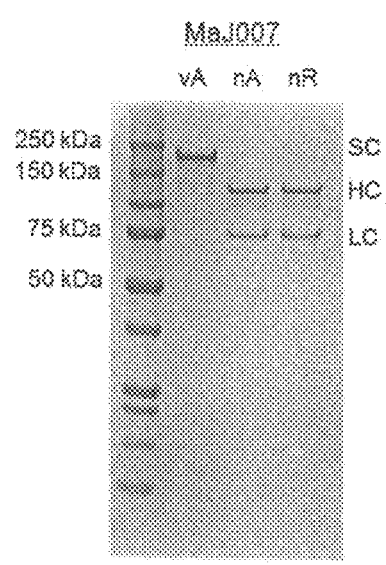

FIG. 2: SDS.PAGE of purified BoNT/A MaJ007 (PAS100-BoNT/A-ISA2-PAS100). Lane 1: Molecular weight marker. Prior to applying the samples to the gel, 1-mercaptoethanol was added. Lane "v.A." (before activation): purified, non-activated single-chain PAS100-BoNT/A-ISA2-PAS100. Lanes "n.A." (after activation) and "n.R." (after purification) show light chain (LC) and heavy chain (HC) obtained after activation by thrombin under reducing conditions.

Figure 3:
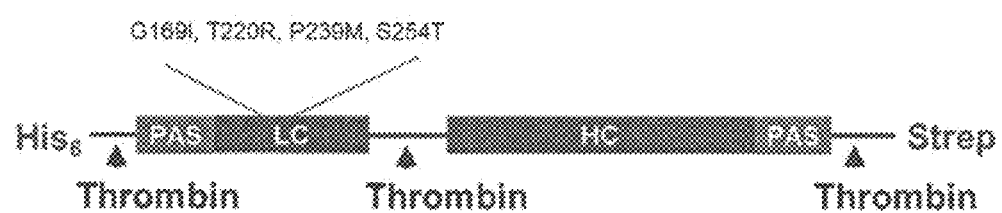

FIG. 3: Schematic Presentation of a modified botulinum toxin PAS100-BoNT/A (G169I, T220R, P239M, S254T)-PAS(100)=PAS100-BoNT/A-ISA5-PAS100), wherein both the light chain (LC) and the heavy chain (HC) each comprise an additional amino acid sequence consisting of 100 amino acid residues, wherein said amino acid sequence consists of proline, alanine and serine residues (PAS) and wherein the light chain (LC) comprises four amino acid modifications are located at the beta-exosite at positions G169, T220, P239, S254, wherein these amino acids are substituted as follows G169I, T220R, P239M, S254T.

Figure 4:
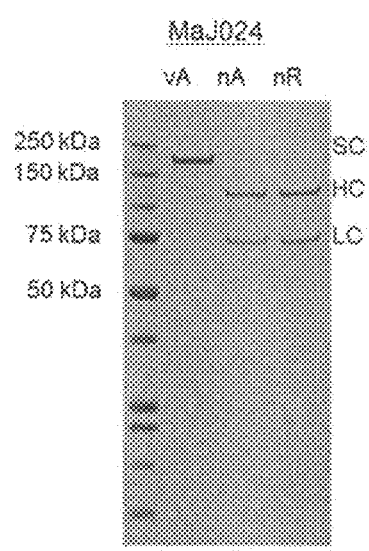

FIG. 4: SDS.PAGE of purified BoNT/A MaJ024 (PAS100-BoNT/A-ISA5-PAS(100). Lane 1: Molecular weight marker. Prior to applying the samples to the gel, 1-mercaptoethanol was added. Lane "v.A." (before activation): purified, non-activated single-chain PAS100-BoNT/A-ISA5-PAS(100. Lanes "n.A." (after activation) and "n.R." (after purification) show light chain (LC) and heavy chain (HC) obtained after activation by thrombin under reducing conditions.

Figure 5:
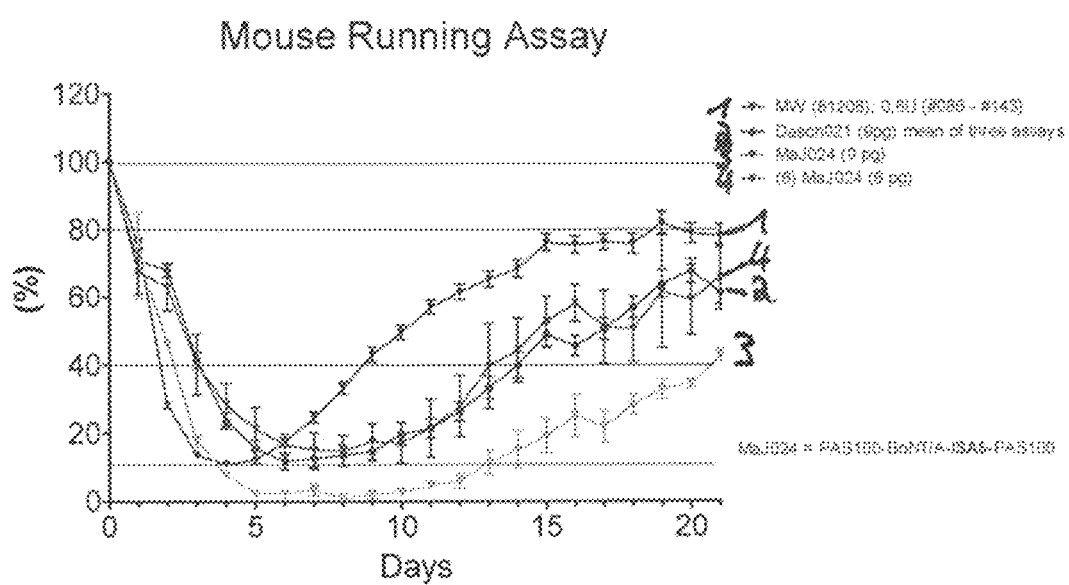

FIG. 5: Mouse running assay with BoNT/A PAS100-BoNT/A-ISA5-PAS100 (MaJ024)

DETAILED DESCRIPTION OF THE INVENTION

The present invention may be understood more readily by reference to the following detailed description of the invention and the examples included therein.

In one aspect, the present invention relates to a recombinant botulinum neurotoxin serotype A comprising at least two domains wherein each domain comprises an amino acid sequence consisting of at least 50 amino acid residues, wherein said amino acid sequence consists of at least one proline, at least one alanine and at least one additional amino acid residue, selected from the group consisting of serine, threonine, tyrosine and glutamine, wherein the neurotoxin further comprises at least one amino acid modification which is located at the alpha-exosite and/or at the beta-exosite of the light chain of the neurotoxin.

In the context of the present invention, the term "botulinum neurotoxin serotype A" refers to a natural neurotoxin serotype A obtainable from bacteria *Clostridium botulinum*, or to a neurotoxin obtainable from alternative sources, including from recombinant technologies or from genetic or chemical modification. Particularly, the botulinum neurotoxins have a specific biological activity, i.e. endopeptidase activity.

Botulinum neurotoxins are produced as single-chain precursors that are proteolytically cleaved by an unknown clostridial endoprotease within the loop region to obtain the biologically active disulfide-linked di-chain form of the neurotoxin, which comprises two chain elements, a functionally active light chain and a functionally active heavy chain, where one end of the light chain is linked to one end of the heavy chain not via a peptide bond, but via a disulfide bond.

In the context of the present invention, the term "botulinum neurotoxin light chain" refers to that part of a botulinum neurotoxin serotype A that comprises an endopeptidase activity responsible for cleaving one or more proteins that is/are part of the so-called SNARE-complex involved in the process resulting in the release of neurotransmitter into the synaptic cleft: In naturally occurring botulinum neurotoxins, the light chain has a molecular weight of approx. 50 kDa.

In the context of the present invention, the term "alpha-exosite of the light chain" refers to four LC alpha-helices (102-113, 310-321, 335-348, and 351-358) that interface a helical motif of SNAP-25 that is approximately 30-50 amino acids away from the cleavage site of SNAP-25 which interacts with the substrate SNAP25 (see Xue S, Javor S, Hixon M S, Janda K D, Probing BoNT/A protease exosites: implications for inhibitor design and light chain longevity. Biochemistry. 2014; 53(43):6820-4).

In the context of the present invention, the term "beta-exosite of the light chain" refers to a beta-sheet region located in a beta-sheet close to the active site which interacts with the substrate SNAP25 comprising AS 162-254 (see Breidenbach M A1, Brunger A T. Substrate recognition strategy for botulinum neurotoxin serotype A, Nature. 2004, 432(7019):925-9).

In the context of the present invention, the term "botulinum neurotoxin heavy chain" refers to that part of a botulinum neurotoxin serotype A that is responsible for entry of the neurotoxin into the neuronal cell: In naturally occurring botulinum neurotoxins, the heavy chain has a molecular weight of approx. 100 kDa.

In the context of the present invention, the term "functionally active botulinum neurotoxin chain" refers to a recombinant botulinum neurotoxin serotype A chain able to perform the biological functions of a naturally occurring botulinum neurotoxin serotype A chain to at least about 50%, particularly to at least about 60%, to at least about 70%, to at least about 80%, and most particularly to at least about 90%, where the biological functions of botulinum neurotoxin chains include, but are not limited to, binding of the heavy chain to the neuronal cell, entry of the neurotoxin into a neuronal cell, release of the light chain from the di-chain neurotoxin, and endopeptidase activity of the light chain. Methods for determining a neurotoxic activity can be found, for example, in WO 95/32738, which describes the reconstitution of separately obtained light and heavy chains of tetanus toxin and botulinum toxin. Also cell-based assay methods as described for example in WO2009/114748, WO 2013/049508 and WO2014/207109.

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the term "recombinant botulinum neurotoxin" refers to a composition comprising a botulinum neurotoxin serotype A that is obtained by expression of the neurotoxin in a heterologous cell such as *E. coli*, and including, but not limited to, the raw material obtained from a fermentation process (supernatant, composition after cell lysis), a fraction comprising a botulinum neurotoxin serotype A obtained from separating the ingredients of such a raw material in a purification process, an isolated and essentially pure protein, and a formulation for pharmaceutical and/or aesthetic use comprising a botulinum neurotoxin serotype A and additionally pharmaceutically acceptable solvents and/or excipients.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In particular embodiments, the recombinant botulinum neurotoxin serotype A according to the invention comprises at least one amino acid modification which is located at the alpha-exosite at at least one position selected from D102, T109, K340, I348, N353, K356.

In particular embodiments, the recombinant botulinum neurotoxin serotype A according to the invention comprises at least one amino acid modification which is located at the beta-exosite at at least one position selected from G169, T220, P239, S254.

In particular embodiments, the recombinant botulinum neurotoxin serotype A according to the invention comprises the following six modifications at the alpha-exosite of the light chain:
  (i) D102F modification (aspartic acid at position 102 of the light chain is replaced by a phenylalanine),
  (ii) T109R modification (threonine at position 109 is replaced by an arginine), (iii) K340M modification (lysine at position 340 is replaced by a methionine), (iv) I348L modification (isoleucine at position 348 of the light chain is replaced by a leucine),
  (v) N353M modification (asparagine at position 353 of the light chain is replaced by a methionine),
  (vi) K356R modification (lysine at position 356 of the light chain is replaced by an arginine).

In particular embodiments, the recombinant botulinum neurotoxin serotype A according to the invention comprises the following four modifications at the beta-exosite of the light chain:
  (i) G169I modification (glycine at position 169 of the light chain is replaced by a isoleucine),
  (ii) T220R modification (threonine at position 220 is replaced by an arginine),
  (iii) P239M modification (proline at position 239 is replaced by a methionine),
  (iv) S254T modification (serine at position 254 of the light chain is replaced by a threonine).

In particular embodiments, the recombinant botulinum neurotoxin serotype A according to the invention comprises two domains wherein each domain comprises an amino acid sequence consisting of between 70 and 260 amino acid residues, particularly 100 amino acid residues, 150 amino acid residues, or 200 amino acid residues, wherein said amino acid sequence consists of at least one proline, at least one alanine and at least one serine residues.

In particular embodiments, the recombinant botulinum neurotoxin serotype A according to the invention comprises two domains wherein each domain comprises an amino acid sequence consisting of between 70 and 150 amino acid residues or between 80 and 120 amino acid residues or between 90 and 110 amino acid residues, wherein said amino acid sequence consists of at least one proline, at least one alanine and at least one serine residues.

In the context of the present invention, the term "functional variant of a botulinum neurotoxin" refers to a botulinum neurotoxin serotype A that differs in the amino acid sequence and/or the nucleic acid sequence encoding the amino acid sequence from a botulinum neurotoxin serotype A, but is still functionally active. In the context of the present invention, the term "functionally active" refers to the property of a recombinant botulinum neurotoxin serotype A to exhibit a biological activity of at least about 20%, particularly to at least about 40%, at least about 70%, at least about 80%, and most particularly at least about 90% of the biological activity of a naturally occurring parental botulinum neurotoxin, i.e. a parental botulinum neurotoxin serotype A without modifications at the C-terminus of the light chain, where the biological functions include, but are not limited to, binding to the neurotoxin receptor, entry of the neurotoxin into a neuronal cell, release of the light chain from the two-chain neurotoxin, and endopeptidase activity of the light chain, and thus inhibition of neurotransmitter release from the affected nerve cell. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressier et al. (Dressler 2005, Mov. Disord. 20:1617-1619, Keller 2006, Neuroscience 139: 629-637) or a cell-based assay as described in WO2009/114748, WO2014/207109 or WO 2013/049508. The biological activity is commonly expressed in Mouse Units (MU). As used herein, 1 MU is the amount of neurotoxin component, which kills 50% of a specified mouse population after intraperitoneal injection, i.e. the mouse i.p. LD50.

On the protein level, a functional variant will maintain key features of the corresponding botulinum neurotoxin serotype A, such as key residues for the endopeptidase activity in the light chain, or key residues for the attachment to the neurotoxin receptors or for translocation through the endosomal membrane in the heavy chain, but may contain modifications comprising a substitution of one or more amino acids of the corresponding botulinum neurotoxin.

In another embodiment, the functional variant of a botulinum neurotoxin serotype A additionally comprises a signal peptide. Usually, said signal peptide will be located at the N-terminus of the neurotoxin. Many such signal peptides are known in the art and are comprised by the present invention. In particular, the signal peptide results in transport of the neurotoxin across a biological membrane, such as the membrane of the endoplasmic reticulum, the Golgi membrane or the plasma membrane of a eukaryotic or prokaryotic cell. It has been found that signal peptides, when attached to the neurotoxin, will mediate secretion of the neurotoxin into the supernatant of the cells. In certain embodiments, the signal peptide will be cleaved off in the course of, or subsequent to, secretion, so that the secreted protein lacks the N-terminal signal peptide, is composed of separate light and heavy chains, which are covalently linked by disulfide bridges, and is proteolytically active.

In particular embodiments, the functional variant has a sequence identity of at least about 40%, at least about 50%, at least about 60%, at least about 70% or most particularly at least about 80%, and a sequence homology of at least about 60%, at least about 70%, at least about 80%, at least about 90%, or most particularly at least about 95% to the corresponding part in the parental botulinum neurotoxin serotype A. Methods and algorithms for determining sequence identity and/or homology, including the comparison of variants having deletions, additions, and/or substitutions relative to a parental sequence, are well known to the practitioner of ordinary skill in the art. The term "identity" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. On the DNA level, the nucleic acid sequences encoding the functional homologue and the parental botulinum neurotoxin may differ to a larger extent due to the degeneracy of the genetic code. It is known that the usage of codons is different between prokaryotic and eukaryotic organisms. Thus, when expressing a prokaryotic protein such as a botulinum neurotoxin, in a eukaryotic expression system, it may be necessary, or at least helpful, to adapt the nucleic acid sequence to the codon usage of the expression host cell, meaning that sequence identity or homology may be rather low on the nucleic acid level.

In the context of the present invention, the term "variant" refers to a botulinum neurotoxin serotype A that is a chemically, enzymatically, or genetically modified derivative of a corresponding neurotoxin of *C. botulinum* neurotoxin serotype A. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids, including modification occurring in the eukaryotic host cell used for expressing the derivative. An enzymatically modified derivative is one that is modified by the activity of enzymes, such as endo- or exoproteolytic enzymes, including modification by enzymes of the eukaryotic host cell used for expressing the derivative. As pointed out above, a genetically modified derivative is one that has been modified by deletion or substitution of one or more amino acids contained in, or by addition of one or more amino acids (including polypeptides comprising between 2 and about 100 amino acids) to, the amino acid sequence of said botulinum neurotoxin. Methods for designing and constructing such chemically or genetically modified derivatives and for testing of such variants for functionality are well known to anyone of ordinary skill in the art.

In particular embodiments, the recombinant botulinum neurotoxin serotype A according to the invention is used in the treatment of a disease requiring improved chemodenervation, wherein the recombinant neurotoxin causes both (i) an increased duration of effect relative to a wildtype botulinum neurotoxin serotype A and (ii) an increased specific biological activity relative to a botulinum neurotoxin serotype A comprising two domains consisting of proline, alanine and serine residues without said modifications in the alpha-exosite and/or at the beta-exosite of the light chain of the neurotoxin.

In the context of the present invention, the term "increased duration of effect" or "increased duration of action" refers to a longer lasting denervation mediated by a botulinum neurotoxin serotype A of the present invention. For example, as disclosed herein, administration of a disulfide-linked di-chain botulinum neurotoxin serotype A comprising two domains according to the invention results in localized paralysis for a longer period of time relative to administration of an identical disulfide-linked di-chain botulinum neurotoxin serotype A without the at least two domains according to the present invention.

In the context of the present invention, the term "increased duration of effect/action" is defined as a more than about 20%, particularly more than about 50%, more particularly more than about 90% increased duration of effect of the recombinant neurotoxin of the present invention relative to the identical neurotoxin without the two domains according to the invention. For example, an "increased duration of effect" can be determined using the "Mouse Running Assay". The "Mouse Running Assay" is well-known to the person skilled in the art and measures the daily running distance of a mouse in a treadmill after a botulinum neurotoxin was injected into the M. gastrocnemius (see Keller J E. Recovery from botulinum neurotoxin poisoning in vivo. Neuroscience. 2006 May 12; 139(2):629-37). The distance which a mouse is able to run in the treadmill the day before the botulinum neurotoxin is injected is used as comparison and is set as 100%. A daily running distance of no more than 80% of the initial running distance is regarded as paralysis of the muscle. The duration of effect is determined by the time period between the time point attaining a half-maximal paralysis, i.e. about 40% of the initial running distance and the time point when paralysis reaches recovery, i.e. 40% of the initial running distance. If this time period is longer than 2 days compared with the standard (wildtype BoNT), the botulinum neurotoxin is considered to exhibit an "increased duration of effect/action" provided that the mutated BoNT exhibits a similar potency i.e shows a similar maximal paralysis (reduction of the running distance) of about 80-90%.

In the context of the present invention, the "specific endoprotease activity" is measured in an assay which is described in Jones et al. (J Immunol Methods. 2008 Jan. 1; 329(1-2):92-101) and Hallis et al. (J Clin Microbiol. 1996 (8):1934-8; 1996) and is described further below in example 2.

In the context of the present invention, the term "decreased specific endoprotease activity" is defined as an at least 20% lower amount of cleavage product produced by a BoNT/A mutant in the endoprotease assay compared to the BoNT/A wildtype applying the same amount of protein.

In the context of the present invention, the term "specific biological activity" relates to the "specific endoprotease activity" mentioned above and can be derived also from the maximal paralysis shown in the "Mouse Running Assay" described above.

In the context of the present invention the term "denervation" refers to denervation resulting from administration of a chemodenervating agent, for example a neurotoxin.

In the context of the present invention, the term "localized denervation" or "localized paralysis" refers to denervation of a particular anatomical region, usually a muscle or a group of anatomically and/or physiologically related muscles, which results from administration of a chemodenervating agent, for example a neurotoxin, to the particular anatomical region.

Without wishing to be bound by theory, the recombinant botulinum neurotoxins of the present invention might show increased biological half-life, reduced degradation rates, decreased diffusion rates, increased uptake by neuronal cells, and/or modified intracellular translocation rates, in each case relative to an identical parental clostridial neurotoxin without the at least two domains according to the invention.

In the context of the present invention, the term "biological half-life" specifies the lifespan of a protein, for example of a botulinum neurotoxin serotype A, in vivo. In the context of the present invention, the term "biological half-life" refers to the period of time, by which half of a protein pool is degraded in vivo. For example it refers to the period of time, by which half of the amount of botulinum neurotoxin of one administered dosage is degraded.

In another aspect, the present invention relates to a composition, in particular a pharmaceutical or cosmetic composition comprising the recombinant botulinum neurotoxin of the present invention. For preparing a preparation comprising a botulinum neurotoxin serotype A the toxin can be formulated by various techniques dependent on the desired application purposes which are known in the art. For example, the (biologically active) botulinum neurotoxin polypeptide can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pa. In an aspect, the pharmaceutical composition can be dissolved in a diluent, prior to administration. The diluent is also selected so as not to affect the biological activity of the Neurotoxin product. Examples of such diluents are distilled water or physiological saline. In addition, the pharmaceutical composition or formulation may also include other carriers or non-toxic, non-therapeutic, non-immunogenic stabilizers and the like. Thus, the formulated Neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. The formulated Neurotoxin product may be used for human or animal therapy of various diseases or disorders in a therapeutically effective dose or for cosmetic purposes.

In particular embodiments, the recombinant botulinum neurotoxin of the present invention or the pharmaceutical composition of the present invention is for use in the treatment of a disease or condition taken from the list of: cervical dystonia (spasmodic torticollis), blepharospasm, severe primary axillary hyperhidrosis, achalasia, lower back pain, benign prostate hypertrophy, chronic focal painful neuropathies, migraine and other headache disorders.

Additional indications where treatment with botulinum neurotoxins is currently under investigation and where the pharmaceutical composition of the present invention may be used, include pediatric incontinence, incontinence due to overactive bladder, and incontinence due to neurogenic bladder, anal fissure, spastic disorders associated with injury or disease of the central nervous system including trauma, stroke, multiple sclerosis, Parkinson's disease, or cerebral palsy, focal dystonias affecting the limbs, face, jaw or vocal cords, temporomandibular joint (TMJ) pain disorders, diabetic neuropathy, wound healing, excessive salivation, vocal cord dysfunction, reduction of the Masseter muscle for decreasing the size of the lower jaw, treatment and prevention of chronic headache and chronic musculoskeletal pain, treatment of snoring noise, assistance in weight loss by increasing the gastric emptying time.

Most recently, clostridial neurotoxins have been evaluated for the treatment of other new indications, for example painful keloid, diabetic neuropathic pain, refractory knee pain, trigeminal neuralgia trigger-zone application to control pain, scarring after cleft-lip surgery, cancer and depression.

In yet another aspect, the present invention relates to the use of the composition of the present invention for cosmetic treatment.

Thus, in another aspect, the present invention relates to a method of cosmetically treating a patient, comprising the step of administering a composition comprising a recombinant clostridial neurotoxin according to the present invention to a patient desiring such cosmetic treatment In the context of the present invention, the term "cosmetic treatment" relates to uses in cosmetic or aesthetic applications, such as the treatment of wrinkles, crow's feet, glabella frown lines, reduction of the masseter muscle, reduction of the calves, removing of facial asymmetries etc.

In another aspect, the present invention relates to a method for the generation of the recombinant botulinum neurotoxin of the present invention, comprising the step of obtaining a recombinant nucleic acid sequence encoding a recombinant single-chain precursor botulinum neurotoxin by the insertion of a nucleic acid sequence encoding at least two domains consisting of proline, alanine and additional amino acid residues, selected from the group consisting of serine, threonine, tyrosine and glutamine residues into a nucleic acid sequence encoding a parental clostridial neurotoxin and by modifying the nucleic acid sequence encoding a parental botulinum neurotoxin at the alpha-exosite and/or at the beta-exosite of the light chain.

In the context of the present invention, the term "recombinant nucleic acid sequence" refers to a nucleic acid, which has been generated by joining genetic material from two different sources.

In the context of the present invention, the term "single-chain precursor botulinum neurotoxin" refers to a single-chain precursor for a disulfide-linked di-chain botulinum neurotoxin, comprising a functionally active botulinum neurotoxin light chain, a functionally active neurotoxin heavy chain, and a loop region linking the C-terminus of the light chain with the N-terminus of the heavy chain.

In the context of the present invention, the term "recombinant single-chain precursor botulinum neurotoxin" refers to a single-chain precursor botulinum neurotoxin comprising at least two domains consisting of proline, alanine and additional amino acid residues, selected from the group consisting of serine, threonine, tyrosine and glutamine residues, and a modified alpha-exosite and/or beta-exosite of the light chain of the neurotoxin.

In particular embodiments, the recombinant single-chain precursor botulinum neurotoxin comprises a protease cleavage site in said loop region.

Single-chain precursor botulinum neurotoxins have to be proteolytically cleaved to obtain the final biologically active botulinum neurotoxins. Proteolytic cleavage may either occur during heterologous expression by host cell enzymes, or by adding proteolytic enzymes to the raw protein material isolated after heterologous expression. Naturally occurring botulinum neurotoxins usually contain one or more cleavage signals for proteases which post-translationally cleave the single-chain precursor molecule, so that the final di- or multimeric complex can form. At present, botulinum neurotoxins are still predominantly produced by fermentation processes using appropriate *Clostridium* strains. During the fermentation process, the single-chain precursors are proteolytically cleaved by an unknown clostridial protease to obtain the biologically active di-chain clostridial neurotoxin. In cases, where the single-chain precursor molecule is the precursor of a protease, autocatalytic cleavage may occur. Alternatively, the protease can be a separate non-clostridial enzyme expressed in the same cell. WO 2006/076902 describes the proteolytic cleavage of a recombinant clostridial neurotoxin single-chain precursor at a heterologous recognition and cleavage site by incubation of the *E. coli* host cell lysate. The proteolytic cleavage is carried out by an unknown *E. coli* protease. In certain applications of recombinant expression, modified protease cleavage sites have been introduced recombinantly into the interchain region between the light and heavy chain of clostridial toxins, e.g. protease cleavage sites for human thrombin or non-human proteases (see WO 01/14570).

In particular embodiments, the protease cleavage site is a site that is cleaved by a protease selected from the list of: thrombin, trypsin, enterokinase, factor Xa, plant papain, insect papain, crustacean papain, enterokinase, human rhinovirus 3C protease, human enterovirus 3C protease, tobacco etch virus protease, Tobacco Vein Mottling Virus, subtilisin and caspase 3.

In a particular embodiment, the recombinant single-chain precursor botulinum neurotoxin serotype A further comprises a binding tag, particularly selected from the group comprising: glutathione-S-transferase (GST), maltose binding protein (MBP), a His-tag, a StrepTag, or a FLAG-tag.

In the context of the present invention, the term "parental botulinum neurotoxin" refers to an initial botulinum neurotoxin without modifications selected from a natural botulinum neurotoxin, a functional variant of a natural botulinum neurotoxin or a chimeric botulinum neurotoxin.

In particular embodiments, the method for the generation of the recombinant botulinum neurotoxin of the present invention further comprises the step of heterologously expressing said recombinant nucleic acid sequence in a host cell, particularly in a bacterial host cell, more particularly in an E. coli host cell.

In certain embodiments, the E. coli cells are selected from E. coli XL1-Blue, Nova Blue, TOP10, XL10-Gold, BL21, and K12.

In particular embodiments, the method for the generation of the recombinant botulinum neurotoxin of the present invention additionally comprises at least one of the steps of (i) generating a disulfide-linked di-chain recombinant botulinum neurotoxin according to the invention by causing or allowing contacting of said recombinant single-chain precursor botulinum neurotoxin with an endoprotease and (ii) purification of said recombinant single-chain precursor botulinum neurotoxin or said disulfide-linked di-chain recombinant botulinum neurotoxin by chromatography.

In particular embodiments, the recombinant single-chain precursor botulinum neurotoxin of the present invention, or the recombinant disulfide-linked di-chain botulinum neurotoxin of the present invention, is purified after expression, or in the case of the recombinant disulfide-linked di-chain botulinum neurotoxin, after the cleavage reaction. In particular such embodiments, the protein is purified by chromatography, particularly by immunoaffinity chromatography, or by chromatography on an ion exchange matrix, a hydrophobic interaction matrix, or a multimodal chromatography matrix, particularly a strong ion exchange matrix, more particularly a strong cation exchange matrix.

In the context of the present invention, the term "causing . . . contacting of said recombinant single-chain precursor botulinum neurotoxin . . . with an endoprotease" refers to an active and/or direct step of bringing said neurotoxin and said endoprotease in contact, whereas the term "allowing contacting of a recombinant single-chain precursor botulinum neurotoxin . . . with an endoprotease" refers to an indirect step of establishing conditions in such a way that said neurotoxin and said endoprotease are getting in contact to each other.

In the context of the present invention, the term "endoprotease" refers to a protease that breaks peptide bonds of non-terminal amino acids (i.e. within the polypeptide chain). As they do not attack terminal amino acids, endoproteases cannot break down peptides into monomers.

In particular embodiments, cleavage of the recombinant single-chain precursor botulinum neurotoxin is near-complete.

In the context of the present invention, the term "near-complete" is defined as more than about 95% cleavage, particularly more than about 97.5%, more particularly more than about 99% as determined by SDS-PAGE and subsequent Western Blot or reversed phase chromatography.

In particular embodiments, cleavage of the recombinant single-chain precursor botulinum neurotoxin of the present invention occurs at a heterologous cleavage signal located in the loop region of the recombinant precursor botulinum neurotoxin.

In particular embodiments, the cleavage reaction is performed with crude host cell lysates containing said single-chain precursor protein.

In other particular embodiments, the single-chain precursor protein is purified or partially purified, particularly by a first chromatographic enrichment step, prior to the cleavage reaction.

In the context of the present invention, the term "purified" relates to more than about 90% purity. In the context of the present invention, the term "partially purified" relates to purity of less than about 90% and an enrichment of more than about two fold.

In another aspect, the present invention relates to a recombinant single-chain botulinum neurotoxin serotype A, which is a precursor for the recombinant botulinum neurotoxin of the present invention. Thus, in such aspect, the present invention relates to a recombinant single-chain precursor botulinum neurotoxin serotype A comprising two domains consisting of proline, alanine and additional amino acid residues, selected from the group consisting of serine, threonine, tyrosine and glutamine residues, and a modified alpha-exosite and/or beta-exosite of the light chain of the neurotoxin.

In another aspect, the present invention relates to a method for obtaining the nucleic acid sequence of the present invention, comprising the step of modifying a nucleic acid sequence encoding a parental botulinum neurotoxin serotype A.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor botulinum neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

EXAMPLES

Example 1: Generation and Purification of a PASylated Botulinum Toxin Type A (PAS100-BoNT/A (D102F T109R K340M I348L N353M K356R)-PAS100)

The nucleic acid construct encoding a "PAS" module comprising 100 amino acid residues built from the amino acids proline (P), alanine (A) and serine (S) was synthetically produced, wherein the following motive was used (ASPAAPAPASPAAPAPSAPA)$_5$. By using restriction enzymes NdeI and SwaI, the corresponding gene module was first inserted at the N-teminus of recombinant BoNT/A (rBoNT/A). In a second step, the PAS module was inserted at the C-terminus of the heavy chain by using restriction enzymes BglII und AatII. The correct cloning was verified by sequencing. For expression of BoNT/A in E. coli gene constructs were cloned into pET29c. The variants contain fused His6- and Strep-affinity tags which can be cleaved after protein purification via thrombin. In order to construct a plasmid for the expression of BoNT/A a synthetic gene with the corresponding mutations of D102F T109R K340M I348L N353M K356R in the BoNT/A1 wild type sequence and restriction sites SwaI and ScaI was used.

Protein Expression and Purification.

Expression of rBoNT/A variants was performed in Riesenberg media with 50 µg/mL Kanamycin{Riesenberg, 1991 #1}. Cells were grown in shake flasks (37° C., 175 r.p.m) until an OD600 of 1.5-2 was reached. For induction of protein expression 1 mM IPTG (Fermentas) was added to the E. coli culture. Protein synthesis was performed for 24 h (15° C., 175 r.p.m.). Cells were collected by centrifugation (5,000 r.p.m., 20 min, 4° C.) and resuspended in His binding buffer pH 8.0 (50 mM Tris, 150 mM NaCl, 5 mM Imidazol) containing EDTA-free protease inhibitor complete (Roche Diagnostics). For the determination of endopeptidase activity and in vivo characterization, the different toxin variants were extracted and purified. Resuspended pellets were disrupted in 2-3 cycles by a French Press Cell Disrupter (Thermo Electron Corporation) at 4° C. The resulting crude extracts were centrifuged (20,000 r.p.m., 30 min, 4° C.), and the supernatants with the soluble proteins were recovered. Protein purification was carried out by fast protein liquid chromatography (GE Healthcare) using a three step purification protocols. The first capture step was performed by IMAC using a HisTrap HP 1 mL column (GE Healthcare). The column was washed (1 ml min-1 working flow) using a two-step protocol with His elution buffer (50 mM Tris, 150 mM NaCl, 400 mM Imidazol pH 8.0). The elution of the toxin proteins occurred at 400 mM Imidazol. In a further step a Strep-Tactin affinity chromatography was performed as previously described (IBA GmbH). As an alternative instead of a second affinity chromatography a cation exchange chromatography with a HiTrap SP HP 1 mL column (GE Healthcare, Freiburg, Germany) was used. The corresponding samples were diluted with SP binding buffer (50 mM Tris, pH 8) and eluted with SP elution buffer (50 mM Tris, 1 M NaCl, pH 8). This procedure was followed by a SEC using a Superdex 200 10/300 column (GE Healthcare). The SEC running buffer (20 mM Tris, 150 mM NaCl, 2.5 mM $CaCl_2$) pH 7.7) was also used to store the purified protein solutions in aliquots at −20° C. Each protein was analyzed by applying 0.5-1 µg on 4-12% gradient SDS-PAGE (Novex Life Technologies) and stained with Coomassie G-250 based SimplyBlue safe stain (Pierce). Each protein was judged >98% pure before applying in vitro or in vivo experiments.

Thrombin Cleavage

BoNT/A preparations were activated with Thrombin (Merck Millipore; 8 U/1 mg BoNT) for 24 h at 20° C. yielding >99% of di-chain toxin. Afterwards the cleavage protease was eliminated with the previously described Strep-Tactin Kit (IBA GmbH).

Expression was performed in expression strain E. coli BI21. Purification was done using a combination of his affinity, ion exchange and size exclusion chromatography, followed by activation using thrombin. FIG. 2 summarizes the results of purification and activation.

Example 2: Determination of Endoproteinase Activity of Wild Type BoNT/A and PASylated BoNT/A The specific endoproteinase activity of wildtype BoNT/A and modified BoNT/A variants was determined by an assay which is described in Jones R G, Ochiai M, Liu Y, Ekong T, Sesardic D. Development of improved SNAP25 endopeptidase immuno-assays for botulinum type A and E toxins. J Immunol Methods. 2008 Jan. 1; 329(1-2):92-101 and Hallis B, James B A, Shone C C Development of novel assays for botulinum type A and B neurotoxins based on their endopeptidase activities. J Clin Microbiol. 1996 (8):1934-8. The "1-step TMB Ultra" solution from Perbio Science was used for staining and quantification. A C-terminal fragment of 70 amino acids of SNAP25 from IBA GmBH was used in the reaction as a substrate. The primary mouse antibody from R&D Systems specifically recognizes SNAP25 fragments cleaved only by BoNT/A. The secondary antibody was an anti-mouse-IgG-HRP-antibody conjugate from Dianova. The assay was performed on a 96 microtiter plate and the amount of cleaved material was determined after 120 minutes by measuring the absorption at 450 nm (Molecular Devices, FilterMax F5). For the assay equal amounts of proteins were used.

The results of the measured endopeptidase activities are shown in the following table 1:

TABLE 1

Endoproteinase activities of mutants

| Batch | Construct | Endopeptidase assay |
|---|---|---|
| Xeomin | Wildtype BoNT/A[#] | 100% |
| DaSch021 | PAS100-BoNT/A-PAS100 | 30-40% |
| MaJ007 | PAS(100)-BoNT/A-ISA2-PA(100) | 85-95% |

ISA2 = (D102F T109R K340M I348L N353M K356R);
[#]Standard

Table 1 shows that the specific endoproteinase activity of PASylated botulinum toxin A was increased by introduced mutations.

Example 3: Generation and Purification of a PASylated Botulinum Toxin Type A (PAS100-BoNT/A G169I, T220R, P239M, S254-PAS100)

The nucleic acid construct encoding a "PAS" module comprising 100 amino acid residues built from the amino acids proline (P), alanine (A) and serine (S) was synthetically produced, wherein the following motive was used (ASPAAPAPASPAAPAPSAPA)$_5$. By using restriction enzymes NdeI and SwaI the corresponding gene module was first inserted at the N-teminus of recombinant BoNT/A (rBoNT/A). In a second step, the PAS module was inserted at the C-terminus of the heavy chain by using restriction enzymes BglII und AatII. The correct cloning was verified by sequencing. For expression of BoNT/A in E. coli gene constructs were cloned into pET29c. The variants contain fused His6- and Strep-affinity tags which can be cleaved after protein purification via thrombin. In order to construct a plasmid for the expression of BoNT/A a synthetic gene with the corresponding mutations of G169I, T220R, P239M, S254 in the BoNT/A1 wild type sequence and restriction sites SwaI and ScaI was used.

Protein expression was performed as described above (see Example 1) in expression strain E. coli BL21. Purification was using a combination of his affinity, ion exchange and size exclusion chromatography, followed by activation using thrombin. FIG. 3 summarizes the results of purification and activation.

Example 4: Duration of Effect of PAS100-BoNT/A (G169I, T220R, P239M, S254T)-PAS100 in the "Mouse Running Assay"

Two different dosages of PAS100-BoNT/A (G169I, T220R, P239M, S254T)-PAS100 (=MaJ024), i.e. 6.0 pg and 9.0 pg were injected into the M. gastrocnemius of each mice in comparison to standard Xeomin® (3 pg; 0.6U) and PASylated Botulinum Toxin Type A without the introduced mutations (=Dasch021). The mice had been trained in a treadmill. The daily running distance in the treadmill was measured over 21 days. The paralysis caused by the toxins was plotted as percentage of the running distance on the day before the injection, which was set as 100%, against the time (see FIG. 5).

As shown in FIG. 5, only 6 pg of PAS100-BoNT/A (G169I, T220R, P239M, S254T)-PAS(100) (=MaJ024) was required to achieve the same paralysis in comparison to 9 pg of Dasch021 (PASylated BoNT/A without introduced mutations) which indicates that the specific potency of MaJ024 was clearly increased in comparison to Dasch021.

TABLE 1

Sequences

SEQ ID NO 1: recombinant BoNT A including His.tag

SEQ ID NO 2: recombinant PAS100-BoNT/A (D102F T109R K340M I348L N353M K356R)-PAS100 including His.tag SEQ ID NO 3: recombinant PAS100-BoNT/A (G169I, T220R, P239M, S254)-PAS100 including His.tag)

SEQ ID NO 4: recombinant PAS100-BoNT/A (D102F T109R K340M I348L N353M K356R)-PAS100 including His.tag (nucleic acid sequence)

SEQ ID NO 5: recombinant PAS100-BoNT/A (G169I, T220R, P239M, S254T)-PAS100 including His.tag) (nucleic acid sequence)

SEQ ID NO 1:
MPFVNKQFNYKDPVNGVDIAYIKIPNAGQMQPVKAFKIHNKIWVIPERDTFTNPEEGDLN
PPPEAKQVPVSYYDSTYLSTDNEKDNYLKGVTKLFERIYSTDLGRMLLTSIVRGIPFWGG
STIDTELKVIDTNCINVIQPDGSYRSEELNLVIIGPSADIIQFECKSFGHEVLNLTRNGY
GSTQYIRFSPDFTFGFEESLEVDTNPLLGAGKFATDPAVTLAHELIHAGHRLYGIAINPN
RVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKV
LNRKTYLNFDKAVFKINIVPKVNYTIYDGFNLRNTNLAANFNGQNTEINNMNFTKLKNFT
GLFEFYKLLCVRGIITSKAGAGKSLVPRGSAGAGALNDLCIKVNNWDLFFSPSEDNFTND
LNKGEEITSDTNIEAAEENISLDLIQQYYLTFNFDNEPENISIENLSSDIIGQLELMPNI
ERFPNGKKYELDKYTMFPHYLRAQEFEHGKSRIALTNSVNEALLNPSRVYTFFSSDYVKKV
NKATEAAMFLGWVEQLVYDFTDETSEVSTTDKIADITIIIPYIGPALNIGNMLYKDDFVG
ALIFSGAVILLEFIPEIAIPVLGTFALVSYIANKVLTVQTIDNALSKRNEKWDEVYKYIV
TNWLAKVNTQIDLIRKKMKEALENQAEATKAIINYQYNQYTEEEKNNINFNIDDLSSKLN
ESINKAMININKFLNQCSVSYLMNSMIPYGVKRLEDFDASLKDALLKYIYDNRGTLIGQV
DRLKDKVNNTLSTDIPFQLSKYVDNQRLLSTFTEYIKNIINTSILNLRYESNHLIDLSRY
ASKINIGSKVNFDPIDKNQIQLFNLESSKIEVILKNAIVYNSMYENFSTSFWIRIPKYFN
SISLNNEYTIINCMENNSGWKVSLNYGEIIWTLQDTQEIKQRVVFKYSQMINISDYINRW
IFVTITNNRLNNSKIYINGRLIDQKPISNLGNIHASNNIMFKLDGCRDTHRYIWIKYFNL
FDKELNEKEIKDLYDNQSNSGILKDFWGDYLQYDKPYYMLNLYDPNKYVDVNNVGIRGYM
YLKGPRGSVMTTNIYLNSSLYRGTKFIIKKYASGNKDNIVRNNDRVYINVVVKNKEYRLA
TNASQAGVEKILSALEIPDVGNLSQVVVMKSKNDQGITNKCKMNLQDNNGNDIGFIGFHQ
FNNIAKLVASNWYNRQIERSSRTLGCSWEFIPVDDGWGERPLGDLVPRGSANSSSVDKLW
SHPQFEKLEHHHHHH

SEQ ID NO 2: recombinant PAS100-BoNT/A (D102F T109R K340M I348L N353M K356R)-PAS100 including His.tag
MGSSHHHHHHGSLVPRSSSASPAAPAPASPAAPAPSAPAASPAAPAPASPAAPAPSAPAA
SPAAPAPASPAAPAPSAPAASPAAPAPASPAAPAPSAPAASPAAPAPASPAAPAPSAPAA
PFVNKQFNYKDPVNGVDIAYIKIPNAGQMQPVKAFKIHNKIWVIPERDTFTNPEEGDLNP
PPEAKQVPVSYYDSTYLSTDNEKDNYLKGVTKLFERIYSTFLGRMLLRSIVRGIPFWGGS
TIDTELKVIDTNCINVIQPDGSYRSEELNLVIIGPSADIIQFECKSFGHEVLNLTRNGYG
STQYIRFSPDFTFGFEESLEVDTNPLLGAGKFATDPAVTLAHELIHAGHRLYGIAINPNR
VFKVNTNAYYEMSGLEVSFEELRTFGGHDAKFIDSLQENEFRLYYYNKFKDIASTLNKAK
SIVGTTASLQYMKNVFKEKYLLSEDTSGKFSVDKLKFDMLYKMLTELYTEDMFVRFFKVL
NRKTYLNFDKAVFKINIVPKVNYTIYDGFNLRNTNLAANFNGQNTEINNMNFTKLKNFTG
LFEFYKLLCVRGIITSKAGAGKSLVPRGSAGAGALNDLCIKVNNWDLFFSPSEDNFTNDL
NKGEEITSDTNIEAAEENISLDLIQQYYLTFNFDNEPENISIENLSSDIIGQLELMPNIE
RFPNGKKYELDKYTMPHYLRAQEFEHGKSRIALTNSVNEALLNPSRVYTFFSSDYVKKVN
KATEAAMFLGWVEQLVYDFTDETSEVSTTDKIADITIIIPYIGPALNIGNMLYKDDFVGA
LIFSGAVILLEFIPEIAIPVLGTFALVSYIANKVLTVQTIDNALSKRNEKWDEVYKYIVT
NWLAKVNTQIDLIRKKMKEALENQAEATKAIINYQYNQYTEEEKNNINFNIDDLSSKLNE
SINKAMININKFLNQCSVSYLMNSMIPYGVKRLEDFDASLKDALLKYIYDNRGTLIGQVD
RLKDKVNNTLSTDIPFQLSKYVDNQRLLSTFTEYIKNIINTSILNLRYESNHLIDLSRYA
SKINIGSKVNFDPIDKNQIQLFNLESSKIEVILKNAIVYNSMYENFSTSFWIRIPKYFNS
ISLNNEYTIINCMENNSGWKVSLNYGEIIWTLQDTQEIKQRVVFKYSQMINISDYINRWI
FVTITNNRLNNSKIYINGRLIDQKPISNLGNIHASNNIMFKLDGCRDTHRYIWIKYFNLF
DKELNEKEIKDLYDNQSNSGILKDFWGDYLQYDKPYYMLNLYDPNKYVDVNNVGIRGYMY
LKGPRGSVMTTNIYLNSSLYRGTKFIIKKYASGNKDNIVRNNDRVYINVVVKNKEYRLAT
NASQAGVEKILSALEIPDVGNLSQVVVMKSKNDQGITNKCKMNLQDNNGNDIGFIGFHQF
NNIAKLVASNWYNRQIERSSRTLGCSWEFIPVDDGWGERPLASPAAPAPASPAAPAPSAP
AASPAAPAPASPAAPAPSAPAASPAAPAPASPAAPAPSAPAASPAAPAPASPAAPAPSAP
AASPAAPAPASPAAPAPSAPAGDLVPRGSANSSSVDKLWSHPQFEK TABLE 1-continued Sequences SEQ ID NO 3: recombinant PAS100-BoNT/A (G169I, T220R, P239M, S254T)-PAS100 including His.tag)
MGSSHHHHHHGSLVPRSSSASPAAPAPASPAAPAPSAPAASPAAPAPASPAAPAPSAPAA
SPAAPAPASPAAPAPSAPAASPAAPAPASPAAPAPSAPAASPAAPAPASPAAPAPSAPAA
PFVNKQFNYKDPVNGVDIAYIKIPNAGQMQPVKAFKIHNKIWVIPERDTFTNPEEGDLNP
PPEAKQVPVSYYDSTYLSTDNEKDNYLKGVTKLFERIYSTDLGRMLLTSIVRGIPFWGGS
TIDTELKVIDTNCINVIQPDGSYRSEELNLVIIGPSADIIQFECKSFIHEVLNLTRNGYG
STQYIRFSPDFTFGFEESLEVDTNPLLGAGKFATDPAVRLAHELIHAGHRLYGIAINMNR
VFKVNTNAYYEMTGLEVSFEELRTFGGHDAKFIDSLQENEFRLYYYNKFKDIASTLNKAK
SIVGTTASLQYMKNVFKEKYLLSEDTSGKFSVDKLKFDKLYKMLTEIYTEDNFVKFFKVL
NRKTYLNFDKAVFKINIVPKVNYTIYDGFNLSNTNLAANFNGQNTEINNMNFTKLKNFTG
LFEFYKLLCVRGIITSKAGAGKSLVPRGSAGAGALNDLCIKVNNWDLFFSPSEDNFTNDL
NKGEEITSDTNIEAAEENISLDLIQQYYLTFNFDNEPENISIENLSSDIIGQLELMPNIE
RFPNGKKYELDKYTMFHYLRAQEFEHGKSRIALTNSVNEALLNPSRVYTFFSSDYVKKVN
KATEAAMFLGWVEQLVYDFTDETSEVSTTDKIADITIIIPYIGPALNIGNMLYKDDFVGA
LIFSGAVILLEFIPEIAIPVLGTFALVSYIANKVLTVQTIDNALSKRNEKWDEVYKYIVT
NWLAKVNTQIDLIRKKMKEALENQAEATKAIINYQYNQYTEEEKNNINFNIDDLSSKLNE
SINKAMININKFLNQCSVSYLMNSMIPYGVKRLEDFDASLKDALLKYIYDNRGTLIGQVD
RLKDKVNNTLSTDIPFQLSKYVDNQRLLSTFTEYIKNIINTSILNLRYESNHLIDLSRYA
SKINIGSKVNFDPIDKNQIQLFNLESSKIEVILKNAIVYNSMYENFSTSFWIRIPKYFNS
ISLNNEYTIINCMENNSGWKVSLNYGEIIWTLQDTQEIKQRVVFKYSQMINISDYINRWI
FVTITNNRLNNSKIYINGRLIDQKPISNLGNIHASNNIMFKLDGCRDTHRYIWIKYFNLF
DKELNEKEIKDLYDNQSNSGILKDFWGDYLQYDKPYYMLNLYDPNKYVDVNNVGIRGYMY
LKGPRGSVMTTNIYLNSSLYRGTKFIIKKYASGNKDNIVRNNDRVYINVVVKNKEYRLAT
NASQAGVEKILSALEIPDVGNLSQVVVMKSKNDQGITNKCKMNLQDNNGNDIGFIGFHQF
NNIAKLVASNWYNRQIERSSRTLGCSWEFIPVDDGWGERPLASPAAPAPASPAAPAPSAP
AASPAAPAPASPAAPAPSAPAASPAAPAPASPAAPAPSAPAASPAAPAPASPAAPAPSAP
AASPAAPAPASPAAPAPSAPAGDLVPRGSANSSSVDKLWSHPQFEK SEQ ID NO 4: recombinant PAS100-BoNT/A (D102F T109R K340M I348L N353M K356R)-PAS100 including His.tag (nucleic acid sequence)
ATGGGTAGCAGCCATCATCATCACCATCATGGTAGCCTTGGTTCCGCGTAGCTCTTCTGCA
AGTCCGGCAGCACCGGCACCGGCTTCACCAGCTGCACCAGCACCTAGCGCACCGGCAGCA
TCTCCAGCAGCCCCTGCACCGGCAAGCCCTGCAGCTCCAGCACCGTCAGCACCAGCAGCA
AGCCCAGCTGCTCCTGCTCCAGCGAGCCCAGCAGCGCCAGCTCCTAGTGCCCCTGCTGCC
TCTCCTGCTGCTCCGGCACCAAGTCCTGCTGCGCCTGCCGAGTGCTCCGGCTGCT
AGTCCTGCCGCACCAGCTCCGGCTAGTCCAGCTGCTCCAGCCCCTTCAGCCCCTGCAGCA
CCATTTGTGAACAAGCAGTTTAACTATAAGGACCCGGTGAACGGTGTGGATATCGCGTAT
ATCAAAATCCCGAATGCGGGCCAGATGCAACCAGTCAAGGCGTTCAAGATTCATAACAAG
ATTTGGGTTATTCCGGAACGTGATACCTTCACCAATCCGGAAGAAGGCGATTTAAATCCG
CCGGCCAGAAGCCAAACAAGTGCCGGTGAGCTACTATGATAGCACGTATCTTAGCACCGAT
AATGAAAAGACAATTACCTGAAGGGCGTGACCAAGTTGTTCGAGCGCATCTACAGTACC
TTCTTAGGCCGCATGTTGTTGCGTAGCATCGTTCGCGGTATCCCGTTCTGGGGCGGCTCG
ACCATTGATACCGAGTTGAAAGTCATTGACACGAACTGTATCAATGTTATCCAACCGGAC
GGCAGTTATCGCAGCGAGGAGTTAAATTTGGTCATCATCGGTCCAAGCGCAGATATTATT
CAGTTCGAATGCAAGAGCTTCGGCCATGAGGTCTTGAATTTGACGCGCAACGGTTACGGC
AGCACCCAATACATCCGCTTTAGCCCGGATTTCACCTTTGGCTTCGAGGAGAGCTTGGAG
GTGGACACCAACCCGCTGTTAGGTGCCGGCAAATTCGCAACCGACCCGGCAGTGACGTTG
GCGCACGAATTGATTCATGCGGGTCACCGCTTATACGGTATCGCGATCAATCCGAATCGC
GTCTTTAAAGTCAATACCAACGCGTACTACGAAATGAGCGGCTTAGAGGTTAGCTTTGAA
GAATTACGCACCTTCGGTGGCCACGACGCCAAGTTCATCGACAGCCTGCAGGAAAATGAG
TTCCGCTTGTACTATTACAATAAATTCAAGGACATCGCGAGCACCTTAAATAAGCAAAG
AGCATTGTGGGCACCACCGCAAGCTTGCAGTACATGAAGAACGTATTTAAGGAAAAATAT
TTGTTGTCGGAGGATACCAGCGGGAAATTCAGCGTCGATAAGCTGAAATTCGACATGTTG
TATAAAATGCTGACCGAGCTGTACACCGAGGATATGTTCGTCCGTTTTTTAAGGTGTTA
AATCGTAAGACCTATTTAAACTTTGATAAAGCGGTGTTTAAAATTAATATCGTGCCGAAG
GTGAATTACACCATCTACGATGGTTTCAATTTACGCAACACGAATCTGGCGGCGAATTTT
AATGGCCAAAACACCGAAATTAACAACATGAACTTTACGAAGTTAAAGAATTTCACGGGC
TTATTCGAATTCTACAAGTTATTATGCGTGCGCGGCATCATTACCAGCAAGGCAGGTGCG
GGCAAGTCCTTGGTTCCGCGTGGCAGCGCCGGCGCCGGCGCGCTCAATGATCTGTGTATT
AAAGTCAATAACTGGGACCTGTTCTTCAGCCCGAGCGAGGATAACTTTACCAACGACTTA
AACAAAGGCGAGGAGATCACGAGCGATACGAACATCGAGGCGGCGGAGGAAATATTAGC
CTGGACCTCATTCAGCAGTACTATCTGACGTTCAATTTTGACAATGAGCCGGAGAACATC
AGCATTGAAAATCTCAGCAGCGACATCATCGGTCAGTTGGAACTGATGCCGAACATTGAA
CGCTTTCCGAACGGCAAAAAATATGAACTGGACAAGTATACCATGTTCCATTACTTACGC
GCACAGGAATTTGAGCACGGCAAGAGCCGCATTGCGCTGACCAATAGCGTTAACGAGGCC
TTGTTAAATCCGAGCCGTGTCTACACGTTCTTCAGCAGCGATTATGTCAAAAAAGTGAAC
AAGGCGACCGAAGCCGCGATGTTTTTGGGCTGGGTCGAGCAATTGGTTTACGATTTTACC
GACGAAACCAGCGAGGTGAGCACGACCGACAAAATTGCAGATATCACCATCATCATTCCG
TACATCGGTCCGGCGCTCAATATCGGCAATATGTTATACAAGGACGACTTTGTGGGCGCG
CTGATCTTTAGCGGCGCGGTTATCTTATTAGAATTCATCCCGGAGATCGCAATCCCGGTC
TTGGGCACCTTTGCGTTGGTGAGCTATATCGCGAATAAAGTGCTCACGGTCCAAACCATC
GATAACGCGCTCAGCAAGCGTAATGAGAAATGGGACGAGGTTTATAAGTATATCGTGACC
AACTGGTTAGCAAAAGTCAATACGCAGATCGATCTCATCCGCAAAAAATGAAAGAAGCC
TTGGAAAATCAAGCGGAGGCAACCAAAGCCATCATTAATTACCAGTATAACCAATATACC
GAAGAAGAAAAAAACAATATCAACTTCAATATCGATGATTTGAGCAGCAAACTGAACGAG
AGCATTAACAAAGCGATGATTAACATCAACAAGTTCTTGAATCAATGCAGCGTGAGCTAT
CTCATGAACAGCATGATCCCGTATGGCGTCAAACGCTTGGAAGATTTTGACGCCAGCCTG TABLE 1-continued Sequences AAAGATGCGCTCCTCAAGTATATTTATGACAACCGCGGCACCCTCATTGGCCAGGTGGAC
CGCTTGAAGGATAAAGTGAACAATACGCTCAGCACGGATATCCCGTTCCAGCTGAGCAAG
TACGTCGACAACCAGCGCTTACTGAGCACCTTTACCGAGTATATCAAGAACATCATTAAT
ACCAGCATCCTCAACTTGCGCTATGAGAGCAATCACCTGATCGACCTCAGCCGCTACGCC
AGCAAGATCAACATCGGCAGCAAGGTCAATTTCGACCCGATCGATAAGAATCAGATCCAA
TTGTTTAACCTGGAAAGCAGCAAGATCGAGGTTATCTTGAAGAACGCGATTGTGTACAAC
AGCATGTACGAGAACTTTAGCACGAGCTTCTGGATTCGTATCCCGAAGTATTTCAATAGC
ATTAGCCTGAATAACGAATATACCATTATCAACTGCATGGAAAATAATAGCGGCTGGAAG
GTGAGCTTAAATTACGGCGAGATCATTTGGACCTTACAGGATACCCAAGAAATCAAACAG
CGCGTCGTCTTTAAGTATAGCCAGATGATCAACATCAGCGATTACATCAACCGCTGGATC
TTCGTGACCATCACCAATAATCGCTTGAATAATAGCAAGATTTACATCAATGGTCGCTTG
ATTGATCAAAAACCGATCAGCAATCTCGGTAATATCCATGCCAGCAATAACATCATGTTT
AAGTTAGACGGTTGCCGCGATACCCACCGCTATATCTGGATCAAGTATTTTAACTTATTT
GATAAGGAACTCAACGAAAAGGAAATTAAAGACTTATATGACAATCAGAGCAATAGCGGC
ATCCTGAAGGATTTCTGGGGCGACTACCTGCAGTACGATAAGCCGTACTATATGTTGAAC
TTGTATGACCCGAACAAATATGTCGATGTGAACAATGTGGGTATTCGTGGCTATATGTAC
TTAAAGGGCCCGCGTGGTAGCGTGATGACCACGAATATTTACTTAAACAGCAGCTTATAC
CGCGGCACGAAGTTTATTATCAAGAAGTATGCCAGCGGCAACAAGGACAATATCGTCCGC
AACAACGACCGTGTGTATATTAACGTGGTGGTGAAGAATAAAGAGTACCGCTTGGCCACG
AATGCGAGCCAGGCGGGCGTGGAAAAAATCTTGAGCGCGTTGGAGATCCCGGACGTCGGC
AACCTCAGCCAGGTTGTGGTGATGAAGTCTAAAAACGACCAGGGCATCACGAACAAGTGC
AAAATGAATTTGCAAGATAACAACGGCAACGACATCGGCTTTATTGGTTTTCACCAGTTC
AATAACATCGCCAAACTCGTGGCCAGCAATTGGTATAACCGCCAAATTGAACGCAGCAGC
CGCACGCTCGGCTGTAGCTGGGAGTTCATCCCGGTGGACGATGGCTGGGGCGAGCGCCCG
CTCGCAAGTCCGGCAGCACCGGCACCGGCTTCACCAGCTGCACCAGCACCTAGCGCACCG
GCAGCATCTCCAGCAGCCCTGCACCGGCAAGCCCTGCAGCTCCAGCACCGTCAGCACCA
GCAGCAAGCCCAGCTGCTCCTGCTCCAGCGAGCCCAGCAGCGCCAGCTCCTAGTGCCCCT
GCTGCCTCTCCTGCTGCTCCGGCACCAGCAAGTCCTGCTGCGCCTGCACCGAGTGCTCCG
GCTGCTAGTCCTGCCGCACCAGCTCCGGCTAGTCCAGCTGCTCCAGCCCCTTCAGCCCCT
GCAGGAGATCTGGTGCCACGCGGTTCCGCGAATTCGAGCTCCGTCGACAAGCTTTGGAGC
CACCCGCAGTTCGAAAAATAA SEQ ID NO 5: recombinant PAS100-BoNT/A (G169I, T220R, P239M,
S254T)-PAS100 including His.tag) (nucleic acid sequence)
ATGGGTAGCAGCCATCATCATCACCATCATGGTAGCCTGGTTCCGCGTAGCTCTTCTGCA
AGTCCGGCAGCACCGGCACCGGCTTCACCAGCTGCACCAGCACCTAGCGCACCGGCACCA
TCTCCAGCAGCCCCTGCACCGGCAAGCCCTGCAGCTCCAGCACCGTCAGCACCAGCAGCA
AGCCCAGCTGCTCCTGCTCCAGCGAGCCCAGCAGCGCCAGCTCCTAGTGCCCCTGCTGCC
TCTCCTGCTGCTCCGGCACCAGCAAGTCCTGCTGCGCCTGCACCGAGTGCTCCGGCTGCT
AGTCCTGCCGCACCAGCTCCGGCTAGTCCAGCTGCTCCAGCCCCTTCAGCCCCTGCAGCA
CCATTTGTGAACAAGCAGTTTAACTATAAGGACCCGGTGAACGGTGTGGATATCGCGTAT
ATCAAAATCCCGAATGCGGGCCAGATGCAACCAGTCAAGGCGTTCAAGATTCATAACAAG
ATTTGGGTTATTCCGGAACGTGATACCTTCACCAATCCGGAAGAAGGCGATTTAAATCCG
CCGCCAGAAGCCAAACAAGTGCCGGTGAGCTACTATGATAGCACGTATCTTAGCACCGAT
AATGAAAAAGACAATTACCTGAAGGGCGTGACCAAGTTGTTCGAGCGCATCTACAGTACC
GACTTAGGCCGCATGTTGTTGACGAGCATCGTTCGCGGTATCCCGTTCTGGGGCGGCTCG
ACCATTGATACCGAGTTGAAAGTCATTGACACGAACTGTATCAATGTTATCCAACCGGAC
GGCAGTTATCGCAGCGAGGAGTTAAATTTGGTCATCATCGGTCCAAGCGCAGATATTATT
CAGTTCGAATGCAAGAGCTTCATCCATGAGGTCTTGAATTTGACGCGCAACGGTTACGGC
AGCACCCAATACATCCGCTTTAGCCCGGATTTCACCTTTGGCTTCGAGGAGAGCTTGGAG
GTGGACACCAACCCGCTGTTAGGTGCCGGCAAATTCGCAACCGACCCGGCAGTGCGCTTG
GCGCACGAATTGATTCATGCGGGTCACCGCTTATACGGTATCGCGATCAATATGAATCGC
GTCTTTAAAGTCAATACCAACGCGTACTACGAAATGACCGGCTTAGAGGTTAGCTTTGAA
GAATTACGCACCTTCGGTGGCCACGACGCCAAGTTCATCGACAGCCTGCAGGAAAATGAG
TTCCGCTTGTACTATTACAATAAATTCAAGGACATCGCGAGCACCTTAAATAAAGCAAAG
AGCATTGTGGGCACCACCGCAAGCTTGCAGTACATGAAGAACGTATTTAAGGAAAAATAT
TTGTTGTCGGAGGATACCAGCGGGAAATTCAGCGTCGATAAGCTGAAATTCGACAAATTG
TATAAAATGCTGACCGAGATTTACACCGAGGATAACTTCGTCAAGTTTTTTAAGGTGTTA
AATCGTAAGACCTATTTAAACTTTGATAAAGCGGTGTTTAAAATTAATATCGTGCCGAAG
GTGAATTACACCATCTACGATGGTTTCAACTTAAGCAACACGAATTCTGGCGGCGAATTT
AATGGCCAAAACACCGAAATTAACAACATGAACTTTACGAAGTTAAAGAATTTCACGGGC
TTATTCGAATTCTACAAGTTATTATGCGTGCGCGGCATCATTACCAGCAAGGCAGGTGCG
GGCAAGTCCTTGGTTCCGCGTGGCAGCGCCGGCGCCGGCGCGCTCAATGATCTGTGTATT
AAAGTCAATAACTGGGACCTGTTCTTCAGCCCGAGCGAGGATAACTTTACCAACGACTTA
AACAAAGGCGAGGAGATCACGAGCGATACGAACATCGAGGCGGCGGAGGAAAATATTAGC
CTGGACCTCATTCAGCAGTACTATCTGACGTTCAATTTTGACAATGAGCCGGAGAACATC
AGCATTGAAAATCTCAGCAGCGACATCATCGGTCAGTTGGAACTGATGCCGAACATTGAA
CGCTTTCCGAACGGCAAAAAATATGAACTGGACAAGTATACCATGTTCCATTACTTACGC
GCACAGGAATTTGAGCACGGCAAGAGCCGCATTGCGCTGACCAATAGCGTTAACGAGGCC
TTGTTAAATCCGAGCCGTGTCTACACGTTCTTCAGCAGCGATTATGTCAAAAAAGTGAAC
AAGGCGACCGAAGCCGCGATGTTTTTGGGCTGGGTCGAGCAATTGGTTTACGATTTTACC
GACGAAACCAGCGAGGTGAGCACGACCGACAAAATTGCAGATATCACCATCATCATTCCG
TACATCGGTCCGGCGCTCAATATCGGCAATATGTTATACAAGGACGACTTTGTGGGCGCG
CTGATCTTTAGCGGCGCGGTTATCTTATTAGAATTCATCCCGGAGATCGCAATCCCGGTC
TTGGGCACCTTTGCGTTGGTGAGCTATATCGCGAATAAAGTGCTCACGGTCCAAACCATC
GATAACGCGCTCAGCAAGCGTAATGAGAAATGGGACGAGGTTTATAAGTATATCGTGACC
AACTGGTTAGCAAAAGTCAATACGCAGATCGATCTCATCCGCAAAAAAATGAAGGAGCC
TTGGAAAATCAAGCGGAGGCAACCAAAGCCATCATTAATTACCAGTATAACCAATATACC TABLE 1-continued Sequences

```
GAAGAAGAAAAAAACAATATCAACTTCAATATCGATGATTTGAGCAGCAAACTGAACGAG
AGCATTAACAAAGCGATGATTAACATCAACAAGTTCTTGAATCAATGCAGCGTGAGCTAT
CTCATGAACAGCATGATCCCGTATGGCGTCAAACGCTTGGAAGATTTTGACGCCAGCCTG
AAAGATGCGCTCCTCAAGTATATTTATGACAACCGCGGCACCCTCATTGGCCAGGTGGAC
CGCTTGAAGGATAAAGTGAACAATACGCTCAGCACGGATATCCCGTTCCAGCTGAGCAAG
TACGTCGACAACCAGCGCTTACTGAGCACCTTTACCGAGTATATCAAGAACATCATTAAT
ACCAGCATCCTCAACTTGCGCTATGAGAGCAATCACCTGATCGACCTCAGCCGCTACGCC
AGCAAGATCAACATCGGCAGCAAGGTCAATTTCGACCCGATCGATAAGAATCAGATCCAA
TTGTTTAACCTGGAAAGCAGCAAGATCGAGGTTATCTTGAAGAACGCGATTGTGTACAAC
AGCATGTACGAGAACTTTAGCACGAGCTTCTGGATTCGTATCCCGAAGTATTTCAATAGC
ATTAGCCTGAATAACGAATATACCATTATCAACTGCATGGAAAATAATAGCGGCTGGAAG
GTGAGCTTAAATTACGGCGAGATCATTTGGACCTTACAGGATACCCAAGAAATCAAACAG
CGCGTCGTCTTTAAGTATAGCCAGATGATCAACATCAGCGATTACATCAACCGCTGGATC
TTCGTGACCATCACCAATAATCGCTTGAATAATAGCAAGATTTACATCAATGGTCGCTTG
ATTGATCAAAAACCGATCAGCAATCTCGGTAATATCCATGCCAGCAATAACATCATGTTT
AAGTTAGACGGTTGCCGCGATACCCACCGCTATATCTGGATCAAGTATTTTAACTTATTT
GATAAGGAACTCAACGAAAAGGAAATTAAAGACTTATATGACAATCAGAGCAATAGCGGC
ATCCTGAAGGATTTCTGGGGCGACTACCTGCAGTACGATAAGCCGTACTATATGTTGAAC
TTGTATGACCCGAACAAATATGTCGATGTGAACAATGTGGGTATTCGTGGCTATATGTAC
TTAAAGGGCCCGCGTGGTAGCGTGATGACCACGAATATTTACTTAAACAGCAGCTTATAC
CGCGGCACGAAGTTTATTATCAAGAAGTATGCCAGCGGCAACAAGGACAATATCGTCCGC
AACAACGACCGTGTGTATATTAACGTGGTGGTGAAGAATAAAGAGTACCGCTTGGCCACG
AATGCGAGCCAGGCGGGCGTGGAAAAAATCTTGAGCGCGTTGGAGATCCCGGACGTCGGC
AACCTCAGCCAGGTTGTGGTGATGAAGTCTAAAAACGACCAGGGCATCACGAACAAGTGC
AAAATGAATTTGCAAGATAACAACGGCAACGACATCGGCTTTATTGGTTTTCACCAGTTC
AATAACATCGCCAAACTCGTGGCCAGCAATTGGTATAACCGCCAAATTGAACGCAGCAGC
CGCACGCTCGGCTGTAGCTGGGAGTTCATCCCGGTGGACGATGGCTGGGGCGAGCGCCCG
CTCGCAAGTCCGGCAGCACCGGCACCGGCTTCACCAGCTGCACCAGCACCTAGCGCACCG
GCAGCATCTCCAGCAGCCCCTGCACCGGCAAGCCCTGCAGCTCCAGCACCGTCAGCACCA
GCAGCAAGCCCAGCTGCTCCTGCTCCAGCGAGCCCAGCAGCGCCAGCTCCTAGTGCCCCT
GCTGCCTCTCCTGCTGCTCCGGCACCAGCAAGTCCTGCTGCGCCTGCACCGAGTGCTCCG
GCTGCTAGTCCTGCCGCACCAGCTCCGGCTAGTCCAGCTGCTCCAGCCCCTTCAGCCCCT
GCAGGAGATCTGGTGCCACGCGGTTCCGCGAATTCGAGCTCCGTCGACAAGCTTTGGAGC
CACCCGCAGTTCGAAAAATAA
```

The invention claimed is:

1. A recombinant botulinum neurotoxin serotype A comprising at least two domains wherein each domain comprises an amino acid sequence comprising at least 50 amino acid residues, wherein said amino acid sequence comprises at least one proline, at least one alanine and at least one additional amino acid residue, selected from the group consisting of serine, threonine, tyrosine and glutamine, wherein the neurotoxin further comprises at least one amino acid modification which is located at the alpha-exosite and/or at the beta-exosite of the light chain of the neurotoxin, wherein the said at least one amino acid modification is located at at least one position selected from D102, T109, K340, I348, N353, and K356 of the alpha-exosite, or at at least one position selected from G169, T220, P239, and S254 of the beta-exosite.

2. The recombinant neurotoxin of claim 1, wherein six amino acid modifications are located at the alpha-exosite at positions D102, T109, K340, I348, N353, K356, wherein these amino acids are substituted as follows D102F, T109R, K340M, I348L, N353M, K356R.

3. The recombinant neurotoxin of claim 1, wherein four amino acid modifications are located at the beta-exosite at positions G169, T220, P239, S254, wherein these amino acids are substituted as follows G169I, T220R, P239M, S254T.

4. The recombinant neurotoxin of claim 2, wherein the neurotoxin comprises two domains wherein each domain comprises an amino acid sequence consisting of between 70 and 260 amino acid residues, wherein said amino acid sequence consists of proline, alanine and serine residues.

5. A composition comprising the recombinant neurotoxin of claim 1 and a solvent or excipient.

6. A pharmaceutical composition comprising the recombinant neurotoxin of claim 1 and one or more pharmaceutically acceptable carriers.

7. A method for the generation of a recombinant neurotoxin according to claim 1, comprising the step of obtaining a recombinant nucleic acid sequence encoding a recombinant single-chain precursor neurotoxin by the insertion of a nucleic acid sequence encoding said at least two domains consisting of proline, alanine and additional amino acid residues, selected from the group consisting of serine, threonine, tyrosine and glutamine residues into a nucleic acid sequence encoding a parental clostridial neurotoxin and by modifying the nucleic acid sequence encoding a parental botulinum neurotoxin at the alpha-exosite and/or at the beta-exosite of the light chain.

8. A recombinant single-chain neurotoxin, which is a precursor for the recombinant neurotoxin of claim 1.

9. A nucleic acid sequence encoding the recombinant single-chain clostridial neurotoxin of claim 8.

10. A vector comprising the nucleic acid sequence of claim 9.

11. A recombinant host cell comprising the nucleic acid sequence of claim 9.

12. A recombinant host cell comprising the vector of claim 10.

13. The recombinant neurotoxin of claim 3, wherein the neurotoxin comprises two domains wherein each domain comprises an amino acid sequence consisting of between 70 and 260 amino acid residues, wherein said amino acid sequence consists of proline, alanine and serine residues.

* * * * *

SEQUENCE LISTING

<160> NUMBER OF SEQ ID NOS: 5

<210> SEQ ID NO 1
<211> LENGTH: 1335
<212> TYPE: PRT
<213> ORGANISM: Artificial Sequence
<220> FEATURE:
<223> OTHER INFORMATION: Synthetic construct

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Ser Thr Ile Asp Thr Glu Leu Lys
        115                 120                 125

```
Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Ala Gly Ala Gly Lys Ser Leu Val Pro Arg
        435                 440                 445

Gly Ser Ala Gly Ala Gly Ala Leu Asn Asp Leu Cys Ile Lys Val Asn
450                 455                 460

Asn Trp Asp Leu Phe Phe Ser Pro Ser Glu Asp Asn Phe Thr Asn Asp
465                 470                 475                 480

Leu Asn Lys Gly Glu Glu Ile Thr Ser Asp Thr Asn Ile Glu Ala Ala
                485                 490                 495

Glu Glu Asn Ile Ser Leu Asp Leu Ile Gln Gln Tyr Tyr Leu Thr Phe
            500                 505                 510

Asn Phe Asp Asn Glu Pro Glu Asn Ile Ser Ile Glu Asn Leu Ser Ser
        515                 520                 525

Asp Ile Ile Gly Gln Leu Glu Leu Met Pro Asn Ile Glu Arg Phe Pro
530                 535                 540
```

```
Asn Gly Lys Lys Tyr Glu Leu Asp Lys Tyr Thr Met Phe His Tyr Leu
545                 550                 555                 560

Arg Ala Gln Glu Phe Glu His Gly Lys Ser Arg Ile Ala Leu Thr Asn
            565                 570                 575

Ser Val Asn Glu Ala Leu Leu Asn Pro Ser Arg Val Tyr Thr Phe Phe
        580                 585                 590

Ser Ser Asp Tyr Val Lys Lys Val Asn Lys Ala Thr Glu Ala Ala Met
    595                 600                 605

Phe Leu Gly Trp Val Glu Gln Leu Val Tyr Asp Phe Thr Asp Glu Thr
610                 615                 620

Ser Glu Val Ser Thr Thr Asp Lys Ile Ala Asp Ile Thr Ile Ile Ile
625                 630                 635                 640

Pro Tyr Ile Gly Pro Ala Leu Asn Ile Gly Asn Met Leu Tyr Lys Asp
                645                 650                 655

Asp Phe Val Gly Ala Leu Ile Phe Ser Gly Ala Val Ile Leu Leu Glu
            660                 665                 670

Phe Ile Pro Glu Ile Ala Ile Pro Val Leu Gly Thr Phe Ala Leu Val
        675                 680                 685

Ser Tyr Ile Ala Asn Lys Val Leu Thr Val Gln Thr Ile Asp Asn Ala
    690                 695                 700

Leu Ser Lys Arg Asn Glu Lys Trp Asp Glu Val Tyr Lys Tyr Ile Val
705                 710                 715                 720

Thr Asn Trp Leu Ala Lys Val Asn Thr Gln Ile Asp Leu Ile Arg Lys
                725                 730                 735

Lys Met Lys Glu Ala Leu Glu Asn Gln Ala Glu Ala Thr Lys Ala Ile
            740                 745                 750

Ile Asn Tyr Gln Tyr Asn Gln Tyr Thr Glu Glu Lys Asn Asn Ile
    755                 760                 765

Asn Phe Asn Ile Asp Asp Leu Ser Ser Lys Leu Asn Glu Ser Ile Asn
770                 775                 780

Lys Ala Met Ile Asn Ile Asn Lys Phe Leu Asn Gln Cys Ser Val Ser
785                 790                 795                 800

Tyr Leu Met Asn Ser Met Ile Pro Tyr Gly Val Lys Arg Leu Glu Asp
                805                 810                 815

Phe Asp Ala Ser Leu Lys Asp Ala Leu Leu Lys Tyr Ile Tyr Asp Asn
            820                 825                 830

Arg Gly Thr Leu Ile Gly Gln Val Asp Arg Leu Lys Asp Lys Val Asn
        835                 840                 845

Asn Thr Leu Ser Thr Asp Ile Pro Phe Gln Leu Ser Lys Tyr Val Asp
    850                 855                 860

Asn Gln Arg Leu Leu Ser Thr Phe Thr Glu Tyr Ile Lys Asn Ile Ile
865                 870                 875                 880

Asn Thr Ser Ile Leu Asn Leu Arg Tyr Glu Ser Asn His Leu Ile Asp
                885                 890                 895

Leu Ser Arg Tyr Ala Ser Lys Ile Asn Ile Gly Ser Lys Val Asn Phe
            900                 905                 910

Asp Pro Ile Asp Lys Asn Gln Ile Gln Leu Phe Asn Leu Glu Ser Ser
        915                 920                 925

Lys Ile Glu Val Ile Leu Lys Asn Ala Ile Val Tyr Asn Ser Met Tyr
    930                 935                 940

Glu Asn Phe Ser Thr Ser Phe Trp Ile Arg Ile Pro Lys Tyr Phe Asn
945                 950                 955                 960
```

Ser Ile Ser Leu Asn Asn Glu Tyr Thr Ile Ile Asn Cys Met Glu Asn
            965                 970                 975

Asn Ser Gly Trp Lys Val Ser Leu Asn Tyr Gly Glu Ile Ile Trp Thr
        980                 985                 990

Leu Gln Asp Thr Gln Glu Ile Lys Gln Arg Val Val Phe Lys Tyr Ser
    995                 1000                1005

Gln Met Ile Asn Ile Ser Asp Tyr Ile Asn Arg Trp Ile Phe Val Thr
1010                1015                1020

Ile Thr Asn Asn Arg Leu Asn Asn Ser Lys Ile Tyr Ile Asn Gly Arg
1025                1030                1035                1040

Leu Ile Asp Gln Lys Pro Ile Ser Asn Leu Gly Asn Ile His Ala Ser
            1045                1050                1055

Asn Asn Ile Met Phe Lys Leu Asp Gly Cys Arg Asp Thr His Arg Tyr
        1060                1065                1070

Ile Trp Ile Lys Tyr Phe Asn Leu Phe Asp Lys Glu Leu Asn Glu Lys
    1075                1080                1085

Glu Ile Lys Asp Leu Tyr Asp Asn Gln Ser Asn Ser Gly Ile Leu Lys
    1090                1095                1100

Asp Phe Trp Gly Asp Tyr Leu Gln Tyr Asp Lys Pro Tyr Tyr Met Leu
1105                1110                1115                1120

Asn Leu Tyr Asp Pro Asn Lys Tyr Val Asp Val Asn Asn Val Gly Ile
            1125                1130                1135

Arg Gly Tyr Met Tyr Leu Lys Gly Pro Arg Gly Ser Val Met Thr Thr
        1140                1145                1150

Asn Ile Tyr Leu Asn Ser Ser Leu Tyr Arg Gly Thr Lys Phe Ile Ile
    1155                1160                1165

Lys Lys Tyr Ala Ser Gly Asn Lys Asp Asn Ile Val Arg Asn Asn Asp
    1170                1175                1180

Arg Val Tyr Ile Asn Val Val Val Lys Asn Lys Glu Tyr Arg Leu Ala
1185                1190                1195                1200

Thr Asn Ala Ser Gln Ala Gly Val Glu Lys Ile Leu Ser Ala Leu Glu
            1205                1210                1215

Ile Pro Asp Val Gly Asn Leu Ser Gln Val Val Val Met Lys Ser Lys
        1220                1225                1230

Asn Asp Gln Gly Ile Thr Asn Lys Cys Lys Met Asn Leu Gln Asp Asn
    1235                1240                1245

Asn Gly Asn Asp Ile Gly Phe Ile Gly Phe His Gln Phe Asn Asn Ile
    1250                1255                1260

Ala Lys Leu Val Ala Ser Asn Trp Tyr Asn Arg Gln Ile Glu Arg Ser
1265                1270                1275                1280

Ser Arg Thr Leu Gly Cys Ser Trp Glu Phe Ile Pro Val Asp Asp Gly
            1285                1290                1295

Trp Gly Glu Arg Pro Leu Gly Asp Leu Val Pro Arg Gly Ser Ala Asn
        1300                1305                1310

Ser Ser Ser Val Asp Lys Leu Trp Ser His Pro Gln Phe Glu Lys Leu
    1315                1320                1325

Glu His His His His His His
    1330                1335

<210> SEQ ID NO 2
<211> LENGTH: 1546
<212> TYPE: PRT
<213> ORGANISM: Artificial Sequence
<220> FEATURE:
<223> OTHER INFORMATION: PAS100-BoNT/A (D102F T109R K340M I348L N353M
     K356R) -PAS100 including His.tag

<400> SEQUENCE: 2

Met Gly Ser Ser His His His His His His Gly Ser Leu Val Pro Arg
1               5                   10                  15

Ser Ser Ser Ala Ser Pro Ala Ala Pro Ala Pro Ala Ser Pro Ala Ala
            20                  25                  30

Pro Ala Pro Ser Ala Pro Ala Ala Ser Pro Ala Ala Pro Ala Pro Ala
            35                  40                  45

Ser Pro Ala Ala Pro Ala Pro Ser Ala Pro Ala Ala Ser Pro Ala Ala
50                  55                  60

Pro Ala Pro Ala Ser Pro Ala Ala Pro Ala Pro Ser Ala Pro Ala Ala
65                  70                  75                  80

Ser Pro Ala Ala Pro Ala Pro Ala Ser Pro Ala Ala Pro Ala Pro Ser
                85                  90                  95

Ala Pro Ala Ala Ser Pro Ala Ala Pro Ala Pro Ala Ser Pro Ala Ala
            100                 105                 110

Pro Ala Pro Ser Ala Pro Ala Ala Pro Phe Val Asn Lys Gln Phe Asn
            115                 120                 125

Tyr Lys Asp Pro Val Asn Gly Val Asp Ile Ala Tyr Ile Lys Ile Pro
130                 135                 140

Asn Ala Gly Gln Met Gln Pro Val Lys Ala Phe Lys Ile His Asn Lys
145                 150                 155                 160

Ile Trp Val Ile Pro Glu Arg Asp Thr Phe Thr Asn Pro Glu Glu Gly
                165                 170                 175

Asp Leu Asn Pro Pro Glu Ala Lys Gln Val Pro Val Ser Tyr Tyr
            180                 185                 190

Asp Ser Thr Tyr Leu Ser Thr Asp Asn Glu Lys Asp Asn Tyr Leu Lys
            195                 200                 205

Gly Val Thr Lys Leu Phe Glu Arg Ile Tyr Ser Thr Phe Leu Gly Arg
210                 215                 220

Met Leu Leu Arg Ser Ile Val Arg Gly Ile Pro Phe Trp Gly Gly Ser
225                 230                 235                 240

Thr Ile Asp Thr Glu Leu Lys Val Ile Asp Thr Asn Cys Ile Asn Val
                245                 250                 255

Ile Gln Pro Asp Gly Ser Tyr Arg Ser Glu Glu Leu Asn Leu Val Ile
            260                 265                 270

Ile Gly Pro Ser Ala Asp Ile Ile Gln Phe Glu Cys Lys Ser Phe Gly
            275                 280                 285

His Glu Val Leu Asn Leu Thr Arg Asn Gly Tyr Gly Ser Thr Gln Tyr
            290                 295                 300

Ile Arg Phe Ser Pro Asp Phe Thr Phe Gly Phe Glu Glu Ser Leu Glu
305                 310                 315                 320

Val Asp Thr Asn Pro Leu Leu Gly Ala Gly Lys Phe Ala Thr Asp Pro
                325                 330                 335

Ala Val Thr Leu Ala His Glu Leu Ile His Ala Gly His Arg Leu Tyr
            340                 345                 350

Gly Ile Ala Ile Asn Pro Asn Arg Val Phe Lys Val Asn Thr Asn Ala
            355                 360                 365

Tyr Tyr Glu Met Ser Gly Leu Glu Val Ser Phe Glu Glu Leu Arg Thr
            370                 375                 380

```
Phe Gly Gly His Asp Ala Lys Phe Ile Asp Ser Leu Gln Glu Asn Glu
385                 390                 395                 400

Phe Arg Leu Tyr Tyr Tyr Asn Lys Phe Lys Asp Ile Ala Ser Thr Leu
            405                 410                 415

Asn Lys Ala Lys Ser Ile Val Gly Thr Thr Ala Ser Leu Gln Tyr Met
            420                 425                 430

Lys Asn Val Phe Lys Glu Lys Tyr Leu Leu Ser Glu Asp Thr Ser Gly
            435                 440                 445

Lys Phe Ser Val Asp Lys Leu Lys Phe Asp Met Leu Tyr Lys Met Leu
            450                 455                 460

Thr Glu Leu Tyr Thr Glu Asp Met Phe Val Arg Phe Phe Lys Val Leu
465                 470                 475                 480

Asn Arg Lys Thr Tyr Leu Asn Phe Asp Lys Ala Val Phe Lys Ile Asn
            485                 490                 495

Ile Val Pro Lys Val Asn Tyr Thr Ile Tyr Asp Gly Phe Asn Leu Arg
            500                 505                 510

Asn Thr Asn Leu Ala Ala Asn Phe Asn Gly Gln Asn Thr Glu Ile Asn
            515                 520                 525

Asn Met Asn Phe Thr Lys Leu Lys Asn Phe Thr Gly Leu Phe Glu Phe
            530                 535                 540

Tyr Lys Leu Leu Cys Val Arg Gly Ile Ile Thr Ser Lys Ala Gly Ala
545                 550                 555                 560

Gly Lys Ser Leu Val Pro Arg Gly Ser Ala Gly Ala Gly Ala Leu Asn
            565                 570                 575

Asp Leu Cys Ile Lys Val Asn Asn Trp Asp Leu Phe Phe Ser Pro Ser
            580                 585                 590

Glu Asp Asn Phe Thr Asn Asp Leu Asn Lys Gly Glu Glu Ile Thr Ser
            595                 600                 605

Asp Thr Asn Ile Glu Ala Ala Glu Gly Asn Ile Ser Leu Asp Leu Ile
            610                 615                 620

Gln Gln Tyr Tyr Leu Thr Phe Asn Phe Asp Asn Glu Pro Glu Asn Ile
625                 630                 635                 640

Ser Ile Glu Asn Leu Ser Ser Asp Ile Ile Gly Gln Leu Glu Leu Met
            645                 650                 655

Pro Asn Ile Glu Arg Phe Pro Asn Gly Lys Lys Tyr Glu Leu Asp Lys
            660                 665                 670

Tyr Thr Met Phe His Tyr Leu Arg Ala Gln Glu Phe Glu His Gly Lys
            675                 680                 685

Ser Arg Ile Ala Leu Thr Asn Ser Val Asn Glu Ala Leu Leu Asn Pro
            690                 695                 700

Ser Arg Val Tyr Thr Phe Phe Ser Ser Asp Tyr Val Lys Lys Val Asn
705                 710                 715                 720

Lys Ala Thr Glu Ala Ala Met Phe Leu Gly Trp Val Glu Gln Leu Val
            725                 730                 735

Tyr Asp Phe Thr Asp Glu Thr Ser Glu Val Ser Thr Thr Asp Lys Ile
            740                 745                 750

Ala Asp Ile Thr Ile Ile Pro Tyr Ile Gly Pro Ala Leu Asn Ile
            755                 760                 765

Gly Asn Met Leu Tyr Lys Asp Asp Phe Val Gly Ala Leu Ile Phe Ser
            770                 775                 780

Gly Ala Val Ile Leu Leu Glu Phe Ile Pro Glu Ile Ala Ile Pro Val
785                 790                 795                 800
```

```
Leu Gly Thr Phe Ala Leu Val Ser Tyr Ile Ala Asn Lys Val Leu Thr
                805                 810                 815

Val Gln Thr Ile Asp Asn Ala Leu Ser Lys Arg Asn Glu Lys Trp Asp
        820                 825                 830

Glu Val Tyr Lys Tyr Ile Val Thr Asn Trp Leu Ala Lys Val Asn Thr
                835                 840                 845

Gln Ile Asp Leu Ile Arg Lys Met Lys Glu Ala Leu Glu Asn Gln
    850                 855                 860

Ala Glu Ala Thr Lys Ala Ile Ile Asn Tyr Gln Tyr Asn Gln Tyr Thr
865                 870                 875                 880

Glu Glu Glu Lys Asn Asn Ile Asn Phe Asn Ile Asp Asp Leu Ser Ser
            885                 890                 895

Lys Leu Asn Glu Ser Ile Asn Lys Ala Met Ile Asn Ile Asn Lys Phe
                900                 905                 910

Leu Asn Gln Cys Ser Val Ser Tyr Leu Met Asn Ser Met Ile Pro Tyr
            915                 920                 925

Gly Val Lys Arg Leu Glu Asp Phe Asp Ala Ser Leu Lys Asp Ala Leu
        930                 935                 940

Leu Lys Tyr Ile Tyr Asp Asn Arg Gly Thr Leu Ile Gly Gln Val Asp
945                 950                 955                 960

Arg Leu Lys Asp Lys Val Asn Asn Thr Leu Ser Thr Asp Ile Pro Phe
                965                 970                 975

Gln Leu Ser Lys Tyr Val Asp Asn Gln Arg Leu Leu Ser Thr Phe Thr
            980                 985                 990

Glu Tyr Ile Lys Asn Ile Ile Asn Thr Ser Ile Leu Asn Leu Arg Tyr
        995                 1000                1005

Glu Ser Asn His Leu Ile Asp Leu Ser Arg Tyr Ala Ser Lys Ile Asn
        1010                1015                1020

Ile Gly Ser Lys Val Asn Phe Asp Pro Ile Asp Lys Asn Gln Ile Gln
1025                1030                1035                1040

Leu Phe Asn Leu Glu Ser Ser Lys Ile Glu Val Ile Leu Lys Asn Ala
                1045                1050                1055

Ile Val Tyr Asn Ser Met Tyr Glu Asn Phe Ser Thr Ser Phe Trp Ile
        1060                1065                1070

Arg Ile Pro Lys Tyr Phe Asn Ser Ile Ser Leu Asn Asn Glu Tyr Thr
        1075                1080                1085

Ile Ile Asn Cys Met Glu Asn Asn Ser Gly Trp Lys Val Ser Leu Asn
        1090                1095                1100

Tyr Gly Glu Ile Ile Trp Thr Leu Gln Asp Thr Gln Glu Ile Lys Gln
1105                1110                1115                1120

Arg Val Val Phe Lys Tyr Ser Gln Met Ile Asn Ile Ser Asp Tyr Ile
                1125                1130                1135

Asn Arg Trp Ile Phe Val Thr Ile Thr Asn Asn Arg Leu Asn Asn Ser
        1140                1145                1150

Lys Ile Tyr Ile Asn Gly Arg Leu Ile Asp Gln Lys Pro Ile Ser Asn
        1155                1160                1165

Leu Gly Asn Ile His Ala Ser Asn Asn Ile Met Phe Lys Leu Asp Gly
        1170                1175                1180

Cys Arg Asp Thr His Arg Tyr Ile Trp Ile Lys Tyr Phe Asn Leu Phe
1185                1190                1195                1200

Asp Lys Glu Leu Asn Glu Lys Glu Ile Lys Asp Leu Tyr Asp Asn Gln
                1205                1210                1215
```

-continued

```
Ser Asn Ser Gly Ile Leu Lys Asp Phe Trp Gly Asp Tyr Leu Gln Tyr
            1220                1225                1230

Asp Lys Pro Tyr Tyr Met Leu Asn Leu Tyr Asp Pro Asn Lys Tyr Val
        1235                1240                1245

Asp Val Asn Asn Val Gly Ile Arg Gly Tyr Met Tyr Leu Lys Gly Pro
    1250                1255                1260

Arg Gly Ser Val Met Thr Thr Asn Ile Tyr Leu Asn Ser Ser Leu Tyr
1265                1270                1275                1280

Arg Gly Thr Lys Phe Ile Ile Lys Lys Tyr Ala Ser Gly Asn Lys Asp
                1285                1290                1295

Asn Ile Val Arg Asn Asn Asp Arg Val Tyr Ile Asn Val Val Val Lys
            1300                1305                1310

Asn Lys Glu Tyr Arg Leu Ala Thr Asn Ala Ser Gln Ala Gly Val Glu
        1315                1320                1325

Lys Ile Leu Ser Ala Leu Glu Ile Pro Asp Val Gly Asn Leu Ser Gln
    1330                1335                1340

Val Val Val Met Lys Ser Lys Asn Asp Gln Gly Ile Thr Asn Lys Cys
1345                1350                1355                1360

Lys Met Asn Leu Gln Asp Asn Asn Gly Asn Asp Ile Gly Phe Ile Gly
                1365                1370                1375

Phe His Gln Phe Asn Asn Ile Ala Lys Leu Val Ala Ser Asn Trp Tyr
            1380                1385                1390

Asn Arg Gln Ile Glu Arg Ser Ser Arg Thr Leu Gly Cys Ser Trp Glu
        1395                1400                1405

Phe Ile Pro Val Asp Asp Gly Trp Gly Glu Arg Pro Leu Ala Ser Pro
    1410                1415                1420

Ala Ala Pro Ala Pro Ala Ser Pro Ala Ala Pro Ala Pro Ser Ala Pro
1425                1430                1435                1440

Ala Ala Ser Pro Ala Ala Pro Ala Pro Ala Ser Pro Ala Ala Pro Ala
                1445                1450                1455

Pro Ser Ala Pro Ala Ala Ser Pro Ala Ala Pro Ala Pro Ala Ser Pro
            1460                1465                1470

Ala Ala Pro Ala Pro Ser Ala Pro Ala Ala Ser Pro Ala Ala Pro Ala
        1475                1480                1485

Pro Ala Ser Pro Ala Ala Pro Ala Pro Ser Ala Pro Ala Ala Ser Pro
    1490                1495                1500

Ala Ala Pro Ala Pro Ala Ser Pro Ala Ala Pro Ala Pro Ser Ala Pro
1505                1510                1515                1520

Ala Gly Asp Leu Val Pro Arg Gly Ser Ala Asn Ser Ser Ser Val Asp
                1525                1530                1535

Lys Leu Trp Ser His Pro Gln Phe Glu Lys
            1540                1545

<210> SEQ ID NO 3
<211> LENGTH: 1546
<212> TYPE: PRT
<213> ORGANISM: Artificial Sequence
<220> FEATURE:
<223> OTHER INFORMATION: PAS100-BoNT/A (G169I, T220R, P239M, S254)
      -PAS100 including His.tag

<400> SEQUENCE: 3

Met Gly Ser Ser His His His His His His Gly Ser Leu Val Pro Arg
1               5                   10                  15

Ser Ser Ser Ala Ser Pro Ala Ala Pro Ala Pro Ala Ser Pro Ala Ala
            20                  25                  30
```

```
Pro Ala Pro Ser Ala Pro Ala Ser Pro Ala Ala Pro Ala
            35                  40                  45

Ser Pro Ala Ala Pro Ala Pro Ser Ala Pro Ala Ala Pro Ala Ala
 50                  55                  60

Pro Ala Pro Ala Ser Pro Ala Ala Pro Ala Pro Ser Ala Pro Ala Ala
 65                  70                  75                  80

Ser Pro Ala Ala Pro Ala Pro Ala Ser Pro Ala Ala Pro Ala Pro Ser
                 85                  90                  95

Ala Pro Ala Ala Ser Pro Ala Ala Pro Ala Ser Pro Ala Ala
                100                 105                 110

Pro Ala Pro Ser Ala Pro Ala Ala Pro Phe Val Asn Lys Gln Phe Asn
            115                 120                 125

Tyr Lys Asp Pro Val Asn Gly Val Asp Ile Ala Tyr Ile Lys Ile Pro
130                 135                 140

Asn Ala Gly Gln Met Gln Pro Val Lys Ala Phe Lys Ile His Asn Lys
145                 150                 155                 160

Ile Trp Val Ile Pro Glu Arg Asp Thr Phe Thr Asn Pro Glu Glu Gly
                165                 170                 175

Asp Leu Asn Pro Pro Glu Ala Lys Gln Val Pro Val Ser Tyr Tyr
                180                 185                 190

Asp Ser Thr Tyr Leu Ser Thr Asp Asn Glu Lys Asp Asn Tyr Leu Lys
            195                 200                 205

Gly Val Thr Lys Leu Phe Glu Arg Ile Tyr Ser Thr Asp Leu Gly Arg
            210                 215                 220

Met Leu Leu Thr Ser Ile Val Arg Gly Ile Pro Phe Trp Gly Gly Ser
225                 230                 235                 240

Thr Ile Asp Thr Glu Leu Lys Val Ile Asp Thr Asn Cys Ile Asn Val
                245                 250                 255

Ile Gln Pro Asp Gly Ser Tyr Arg Ser Glu Glu Leu Asn Leu Val Ile
            260                 265                 270

Ile Gly Pro Ser Ala Asp Ile Ile Gln Phe Glu Cys Lys Ser Phe Ile
            275                 280                 285

His Glu Val Leu Asn Leu Thr Arg Asn Gly Tyr Gly Ser Thr Gln Tyr
            290                 295                 300

Ile Arg Phe Ser Pro Asp Phe Thr Phe Gly Phe Glu Glu Ser Leu Glu
305                 310                 315                 320

Val Asp Thr Asn Pro Leu Leu Gly Ala Gly Lys Phe Ala Thr Asp Pro
                325                 330                 335

Ala Val Arg Leu Ala His Glu Leu Ile His Ala Gly His Arg Leu Tyr
            340                 345                 350

Gly Ile Ala Ile Asn Met Asn Arg Val Phe Lys Val Asn Thr Asn Ala
            355                 360                 365

Tyr Tyr Glu Met Thr Gly Leu Glu Val Ser Phe Glu Glu Leu Arg Thr
            370                 375                 380

Phe Gly Gly His Asp Ala Lys Phe Ile Asp Ser Leu Gln Glu Asn Glu
385                 390                 395                 400

Phe Arg Leu Tyr Tyr Tyr Asn Lys Phe Lys Asp Ile Ala Ser Thr Leu
                405                 410                 415

Asn Lys Ala Lys Ser Ile Val Gly Thr Thr Ala Ser Leu Gln Tyr Met
            420                 425                 430

Lys Asn Val Phe Lys Glu Lys Tyr Leu Leu Ser Glu Asp Thr Ser Gly
            435                 440                 445
```

-continued

```
Lys Phe Ser Val Asp Lys Leu Lys Phe Asp Lys Leu Tyr Lys Met Leu
    450                 455                 460

Thr Glu Ile Tyr Thr Glu Asp Asn Phe Val Lys Phe Lys Val Leu
465                 470                 475                 480

Asn Arg Lys Thr Tyr Leu Asn Phe Asp Lys Ala Val Phe Lys Ile Asn
                    485                 490                 495

Ile Val Pro Lys Val Asn Tyr Thr Ile Tyr Asp Gly Phe Asn Leu Ser
                500                 505                 510

Asn Thr Asn Leu Ala Ala Asn Phe Asn Gly Gln Asn Thr Glu Ile Asn
                515                 520                 525

Asn Met Asn Phe Thr Lys Leu Lys Asn Phe Thr Gly Leu Phe Glu Phe
530                 535                 540

Tyr Lys Leu Leu Cys Val Arg Gly Ile Ile Thr Ser Lys Ala Gly Ala
545                 550                 555                 560

Gly Lys Ser Leu Val Pro Arg Gly Ser Ala Gly Ala Gly Ala Leu Asn
                565                 570                 575

Asp Leu Cys Ile Lys Val Asn Asn Trp Asp Leu Phe Phe Ser Pro Ser
                580                 585                 590

Glu Asp Asn Phe Thr Asn Asp Leu Asn Lys Gly Glu Glu Ile Thr Ser
            595                 600                 605

Asp Thr Asn Ile Glu Ala Ala Glu Glu Asn Ile Ser Leu Asp Leu Ile
            610                 615                 620

Gln Gln Tyr Tyr Leu Thr Phe Asn Phe Asp Asn Glu Pro Glu Asn Ile
625                 630                 635                 640

Ser Ile Glu Asn Leu Ser Ser Asp Ile Ile Gly Gln Leu Glu Leu Met
                645                 650                 655

Pro Asn Ile Glu Arg Phe Pro Asn Gly Lys Lys Tyr Glu Leu Asp Lys
                660                 665                 670

Tyr Thr Met Phe His Tyr Leu Arg Ala Gln Glu Phe Glu His Gly Lys
                675                 680                 685

Ser Arg Ile Ala Leu Thr Asn Ser Val Asn Glu Ala Leu Leu Asn Pro
690                 695                 700

Ser Arg Val Tyr Thr Phe Phe Ser Ser Asp Tyr Val Lys Lys Val Asn
705                 710                 715                 720

Lys Ala Thr Glu Ala Ala Met Phe Leu Gly Trp Val Glu Gln Leu Val
                725                 730                 735

Tyr Asp Phe Thr Asp Glu Thr Ser Glu Val Ser Thr Thr Asp Lys Ile
                740                 745                 750

Ala Asp Ile Thr Ile Ile Pro Tyr Ile Gly Pro Ala Leu Asn Ile
                755                 760                 765

Gly Asn Met Leu Tyr Lys Asp Asp Phe Val Gly Ala Leu Ile Phe Ser
                770                 775                 780

Gly Ala Val Ile Leu Leu Glu Phe Ile Pro Glu Ile Ala Ile Pro Val
785                 790                 795                 800

Leu Gly Thr Phe Ala Leu Val Ser Tyr Ile Ala Asn Lys Val Leu Thr
                805                 810                 815

Val Gln Thr Ile Asp Asn Ala Leu Ser Lys Arg Asn Glu Lys Trp Asp
                820                 825                 830

Glu Val Tyr Lys Tyr Ile Val Thr Asn Trp Leu Ala Lys Val Asn Thr
                835                 840                 845

Gln Ile Asp Leu Ile Arg Lys Lys Met Lys Glu Ala Leu Glu Asn Gln
850                 855                 860
```

```
Ala Glu Ala Thr Lys Ala Ile Ile Asn Tyr Gln Tyr Asn Gln Tyr Thr
865                 870                 875                 880

Glu Glu Glu Lys Asn Asn Ile Asn Phe Asn Ile Asp Asp Leu Ser Ser
                885                 890                 895

Lys Leu Asn Glu Ser Ile Asn Lys Ala Met Ile Asn Ile Asn Lys Phe
            900                 905                 910

Leu Asn Gln Cys Ser Val Ser Tyr Leu Met Asn Ser Met Ile Pro Tyr
            915                 920                 925

Gly Val Lys Arg Leu Glu Asp Phe Asp Ala Ser Leu Lys Asp Ala Leu
            930                 935                 940

Leu Lys Tyr Ile Tyr Asp Asn Arg Gly Thr Leu Ile Gly Gln Val Asp
945                 950                 955                 960

Arg Leu Lys Asp Lys Val Asn Asn Thr Leu Ser Thr Asp Ile Pro Phe
                965                 970                 975

Gln Leu Ser Lys Tyr Val Asp Asn Gln Arg Leu Leu Ser Thr Phe Thr
            980                 985                 990

Glu Tyr Ile Lys Asn Ile Ile Asn Thr Ser Ile Leu Asn Leu Arg Tyr
            995                 1000                1005

Glu Ser Asn His Leu Ile Asp Leu Ser Arg Tyr Ala Ser Lys Ile Asn
    1010                1015                1020

Ile Gly Ser Lys Val Asn Phe Asp Pro Ile Asp Lys Asn Gln Ile Gln
1025                1030                1035                1040

Leu Phe Asn Leu Glu Ser Ser Lys Ile Glu Val Ile Leu Lys Asn Ala
                1045                1050                1055

Ile Val Tyr Asn Ser Met Tyr Glu Asn Phe Ser Thr Ser Phe Trp Ile
            1060                1065                1070

Arg Ile Pro Lys Tyr Phe Asn Ser Ile Ser Leu Asn Asn Glu Tyr Thr
            1075                1080                1085

Ile Ile Asn Cys Met Glu Asn Asn Ser Gly Trp Lys Val Ser Leu Asn
            1090                1095                1100

Tyr Gly Glu Ile Ile Trp Thr Leu Gln Asp Thr Gln Glu Ile Lys Gln
1105                1110                1115                1120

Arg Val Val Phe Lys Tyr Ser Gln Met Ile Asn Ile Ser Asp Tyr Ile
            1125                1130                1135

Asn Arg Trp Ile Phe Val Thr Ile Thr Asn Asn Arg Leu Asn Asn Ser
            1140                1145                1150

Lys Ile Tyr Ile Asn Gly Arg Leu Ile Asp Gln Lys Pro Ile Ser Asn
            1155                1160                1165

Leu Gly Asn Ile His Ala Ser Asn Asn Ile Met Phe Lys Leu Asp Gly
    1170                1175                1180

Cys Arg Asp Thr His Arg Tyr Ile Trp Ile Lys Tyr Phe Asn Leu Phe
1185                1190                1195                1200

Asp Lys Glu Leu Asn Glu Lys Glu Ile Lys Asp Leu Tyr Asp Asn Gln
                1205                1210                1215

Ser Asn Ser Gly Ile Leu Lys Asp Phe Trp Gly Asp Tyr Leu Gln Tyr
            1220                1225                1230

Asp Lys Pro Tyr Tyr Met Leu Asn Leu Tyr Asp Pro Asn Lys Tyr Val
            1235                1240                1245

Asp Val Asn Asn Val Gly Ile Arg Gly Tyr Met Tyr Leu Lys Gly Pro
    1250                1255                1260

Arg Gly Ser Val Met Thr Thr Asn Ile Tyr Leu Asn Ser Ser Leu Tyr
1265                1270                1275                1280
```

-continued

```
Arg Gly Thr Lys Phe Ile Ile Lys Lys Tyr Ala Ser Gly Asn Lys Asp
                1285                1290                1295

Asn Ile Val Arg Asn Asn Asp Arg Val Tyr Ile Asn Val Val Val Lys
            1300                1305                1310

Asn Lys Glu Tyr Arg Leu Ala Thr Asn Ala Ser Gln Ala Gly Val Glu
        1315                1320                1325
Lys Ile Leu Ser Ala Leu Glu Ile Pro Asp Val Gly Asn Leu Ser Gln
    1330                1335                1340

Val Val Val Met Lys Ser Lys Asn Asp Gln Gly Ile Thr Asn Lys Cys
1345                1350                1355                1360
Lys Met Asn Leu Gln Asp Asn Asn Gly Asn Asp Ile Gly Phe Ile Gly
                1365                1370                1375

Phe His Gln Phe Asn Asn Ile Ala Lys Leu Val Ala Ser Asn Trp Tyr
            1380                1385                1390
Asn Arg Gln Ile Glu Arg Ser Ser Arg Thr Leu Gly Cys Ser Trp Glu
        1395                1400                1405

Phe Ile Pro Val Asp Asp Gly Trp Gly Glu Arg Pro Leu Ala Ser Pro
    1410                1415                1420

Ala Ala Pro Ala Pro Ala Ser Pro Ala Ala Pro Ala Pro Ser Ala Pro
1425                1430                1435                1440
Ala Ala Ser Pro Ala Ala Pro Ala Pro Ala Ser Pro Ala Ala Pro Ala
                1445                1450                1455

Pro Ser Ala Pro Ala Ala Ser Pro Ala Ala Pro Ala Pro Ala Ser Pro
            1460                1465                1470
Ala Ala Pro Ala Pro Ser Ala Pro Ala Ala Ser Pro Ala Ala Pro Ala
        1475                1480                1485

Pro Ala Ser Pro Ala Ala Pro Ala Pro Ser Ala Pro Ala Ala Ser Pro
    1490                1495                1500

Ala Ala Pro Ala Pro Ala Ser Pro Ala Ala Pro Ala Pro Ser Ala Pro
1505                1510                1515                1520
Ala Gly Asp Leu Val Pro Arg Gly Ser Ala Asn Ser Ser Ser Val Asp
                1525                1530                1535

Lys Leu Trp Ser His Pro Gln Phe Glu Lys
            1540                1545

<210> SEQ ID NO 4
<211> LENGTH: 4641
<212> TYPE: DNA
<213> ORGANISM: Artificial Sequence
<220> FEATURE:
<223> OTHER INFORMATION: PAS100-BoNT/A (D102F T109R K340M I348L N353M
      K356R) -PAS100 including His.tag (nucleic acid sequence)

<400> SEQUENCE: 4
atgggtagca gccatcatca tcaccatcat ggtagcctgg ttccgcgtag ctcttctgca     60
agtccggcag caccggcacc ggcttcacca gctgcaccag cacctagcgc accggcagca    120
tctccagcag cccctgcacc ggcaagccct gcagctccag caccgtcagc accagcagca    180
agcccagctg ctcctgctcc agcgagccca gcagcgccag ctcctagtgc ccctgctgcc    240
tctcctgctg ctccggcacc agcaagtcct gctgcgcctg caccgagtgc tccggctgct    300
agtcctgccg caccagctcc ggctagtcca gctgctccag ccccttcagc ccctgcagca    360
ccatttgtga acaagcagtt taactataag gacccggtga acggtgtgga tatcgcgtat    420
atcaaaatcc cgaatgcggg ccagatgcaa ccagtcaagg cgttcaagat tcataacaag    480
atttgggtta ttccggaacg tgataccttc accaatccgg aagaaggcga tttaaatccg    540
```

```
ccgccagaag ccaaacaagt gccggtgagc tactatgata gcacgtatct tagcaccgat    600
aatgaaaaag acaattacct gaagggcgtg accaagttgt tcgagcgcat ctacagtacc    660
ttcttaggcc gcatgttgtt gcgtagcatc gttcgcggta tcccgttctg gggcggctcg    720
accattgata ccgagttgaa agtcattgac acgaactgta tcaatgttat ccaaccggac    780
ggcagttatc gcagcgagga gttaaatttg gtcatcatcg gtccaagcgc agatattatt    840
cagttcgaat gcaagagctt cggccatgag gtcttgaatt tgacgcgcaa cggttacggc    900
agcacccaat acatccgctt tagcccggat ttcacctttg gcttcgagga gagcttggag    960
gtggacacca cccgctgtt aggtgccggc aaattcgcaa ccgacccggc agtgacgttg   1020
gcgcacgaat tgattcatgc gggtcaccgc ttatacggta tcgcgatcaa tccgaatcgc   1080
gtctttaaag tcaataccaa cgcgtactac gaaatgagcg gcttagaggt tagctttgaa   1140
gaattacgca ccttcggtgg ccacgacgcc aagttcatcg acagcctgca ggaaaatgag   1200
ttccgcttgt actattacaa taaattcaag gacatcgcga gcaccttaaa taaagcaaag   1260
agcattgtgg gcaccaccgc aagcttgcag tacatgaaga acgtatttaa ggaaaaatat   1320
ttgttgtcgg aggataccag cgggaaattc agcgtcgata agctgaaatt cgacatgttg   1380
tataaaatgc tgaccgagct gtacaccgag gatatgttcg tccgtttttt taaggtgtta   1440
aatcgtaaga cctatttaaa ctttgataaa gcggtgttta aaattaatat cgtgccgaag   1500
gtgaattaca ccatctacga tggtttcaat ttacgcaaca cgaatctggc ggcgaatttt   1560
aatggccaaa acaccgaaat taacaacatg aactttacga agttaaagaa tttcacgggc   1620
ttattcgaat tctacaagtt attatgcgtg cgcggcatca ttaccagcaa ggcaggtgcg   1680
ggcaagtcct tggttccgcg tggcagcgcc ggcgccggcg cgctcaatga tctgtgtatt   1740
aaagtcaata actgggacct gttccttcagc ccgagcgagg ataactttac caacgactta   1800
aacaaaggcg aggagatcac gagcgatacg aacatcgagg cggcggagga aaatattagc   1860
ctggacctca ttcagcagta ctatctgacg ttcaattttg acaatgagcc ggagaacatc   1920
agcattgaaa atctcagcag cgacatcatc ggtcagttgg aactgatgcc gaacattgaa   1980
cgcttttccga acggcaaaaa atatgaactg gacaagtata ccatgttcca ttacttacgc   2040
gcacaggaat ttgagcacgg caagagccgc attgcgctga ccaatagcgt taacgaggcc   2100
ttgttaaatc cgagccgtgt ctacacgttc ttcagcagcg attatgtcaa aaaagtgaac   2160
aaggcgaccg aagccgcgat gttttggggc tgggtcgagc aattggttta cgattttacc   2220
gacgaaacca gcgaggtgag cacgaccgac aaaattgcag atatcaccat catcattccg   2280
tacatcggtc cggcgctcaa tatcggcaat atgttataca aggacgactt tgtgggcgcg   2340
ctgatcttta gcgcgcggt tatcttatta gaattcatcc cggagatcgc aatcccggtc   2400
ttgggcacct ttgcgttggt gagctatatc gcgaataaag tgctcacggt ccaaaccatc   2460
gataacgcgc tcagcaagcg taatgagaaa tgggacgagg tttataagta tatcgtgacc   2520
aactggttag caaaagtcaa tacgcagatc gatctcatcc gcaaaaaaat gaaagaagcc   2580
ttggaaaatc aagcggaggc aaccaaagcc atcattaatt accagtataa ccaatatacc   2640
gaagaagaaa aaacaatat caacttcaat atcgatgatt tgagcagcaa actgaacgag   2700
agcattaaca aagcgatgat taacatcaac aagttcttga atcaatgcag cgtgagctat   2760
ctcatgaaca gcatgatccc gtatggcgtc aaacgcttgg aagattttga cgccagcctg   2820
aaagatcgcg tcctcaagta tatttatgac aaccgcggca ccctcattgg ccaggtggac   2880
cgcttgaagg ataaagtgaa caatacgctc agcacggata tcccgttcca gctgagcaag   2940
```

-continued

```
tacgtcgaca accagcgctt actgagcacc tttaccgagt atatcaagaa catcattaat   3000
accagcatcc tcaacttgcg ctatgagagc aatcacctga tcgacctcag ccgctacgcc   3060
agcaagatca acatcggcag caaggtcaat ttcgacccga tcgataagaa tcagatccaa   3120
ttgtttaacc tggaaagcag caagatcgag gttatcttga agaacgcgat tgtgtacaac   3180
agcatgtacg agaactttag cacgagcttc tggattcgta tcccgaagta tttcaatagc   3240
attagcctga ataacgaata taccattatc aactgcatgg aaaataatag cggctggaag   3300
gtgagcttaa attacggcga gatcatttgg accttacagg atacccaaga aatcaaacag   3360
cgcgtcgtct ttaagtatag ccagatgatc aacatcagcg attacatcaa ccgctggatc   3420
ttcgtgacca tcaccaataa tcgcttgaat aatagcaaga tttacatcaa tggtcgcttg   3480
attgatcaaa aaccgatcag caatctcggt aatatccatg ccagcaataa catcatgttt   3540
aagttagacg gttgccgcga tacccaccgc tatatctgga tcaagtattt taacttattt   3600
gataaggaac tcaacgaaaa ggaaattaaa gacttatatg acaatcagag caatagcggc   3660
atcctgaagg atttctgggg cgactacctg cagtacgata agccgtacta tatgttgaac   3720
ttgtatgacc cgaacaaata tgtcgatgtg aacaatgtgg gtattcgtgg ctatatgtac   3780
ttaaagggcc cgcgtggtag cgtgatgacc acgaatattt acttaaacag cagcttatac   3840
cgcggcacga agtttattat caagaagtat gccagcggca acaaggacaa tatcgtccgc   3900
aacaacgacc gtgtgtatat taacgtggtg gtgaagaata aagagtaccg cttggccacg   3960
aatgcgagcc aggcgggcgt ggaaaaaatc ttgagcgcgt tggagatccc ggacgtcggc   4020
aacctcagcc aggttgtggt gatgaagtct aaaaacgacc agggcatcac gaacaagtgc   4080
aaaatgaatt tgcaagataa caacggcaac gacatcggct ttattggttt tcaccagttc   4140
aataacatcg ccaaactcgt ggccagcaat tggtataacc gccaaattga acgcagcagc   4200
cgcacgctcg gctgtagctg ggagttcatc ccggtggacg atggctgggg cgagcgcccg   4260
ctcgcaagtc cggcagcacc ggcaccggct tcaccagctg caccagcacc tagcgcaccg   4320
gcagcatctc cagcagcccc tgcaccggca agccctgcag ctccagcacc gtcagcacca   4380
gcagcaagcc cagctgctcc tgctccagcg agcccagcag cgccagctcc tagtgcccct   4440
gctgcctctc ctgctgctcc ggcaccagca agtcctgctg cgcctgcacc gagtgctccg   4500
gctgctagtc ctgccgcacc agctccggct agtccagctg ctccagcccc ttcagcccct   4560
gcaggagatc tggtgccacg cggttccgcg aattcgagct ccgtcgacaa gctttggagc   4620
cacccgcagt tcgaaaaata a                                             4641
```

```
<210> SEQ ID NO 5
<211> LENGTH: 4641
<212> TYPE: DNA
<213> ORGANISM: Artificial Sequence
<220> FEATURE:
<223> OTHER INFORMATION: PAS100-BoNT/A (G169I, T220R, P239M, S254T)
      -PAS100 including His.tag) (nucleic acid sequence)

<400> SEQUENCE: 5
```

```
atgggtagca gccatcatca tcaccatcat ggtagcctgg ttccgcgtag ctcttctgca     60
agtccggcag caccggcacc ggcttcacca gctgcaccag cacctagcgc accggcagca    120
tctccagcag cccctgcacc ggcaagccct gcagctccag caccgtcagc accagcagca    180
agcccagctg ctcctgctcc agcgagccca gcagcgccag ctcctagtgc ccctgctgcc    240
tctcctgctg ctccggcacc agcaagtcct gctgcgcctg caccgagtgc tccggctgct    300
```

```
agtcctgccg caccagctcc ggctagtcca gctgctccag cccttcagc ccctgcagca    360
ccatttgtga caagcagtt taactataag gacccggtga acggtgtgga tatcgcgtat    420
atcaaaatcc cgaatgcggg ccagatgcaa ccagtcaagg cgttcaagat tcataacaag    480
atttgggtta ttccggaacg tgataccttc accaatccgg aagaaggcga tttaaatccg    540
ccgccagaag ccaaacaagt gccggtgagc tactatgata gcacgtatct tagcaccgat    600
aatgaaaaag acaattacct gaagggcgtg accaagttgt tcgagcgcat ctacagtacc    660
gacttaggcc gcatgttgtt gacgagcatc gttcgcggta tcccgttctg gggcggctcg    720
accattgata ccgagttgaa agtcattgac acgaactgta tcaatgttat ccaaccggac    780
ggcagttatc gcagcgagga gttaaatttg gtcatcatcg gtccaagcgc agatattatt    840
cagttcgaat gcaagagctt catccatgag gtcttgaatt tgacgcgcaa cggttacggc    900
agcacccaat acatccgctt tagcccggat ttcacctttg gcttcgagga gagcttggag    960
gtggacacca acccgctgtt aggtgccggc aaattcgcaa ccgacccggc agtgcgcttg   1020
gcgcacgaat tgattcatgc gggtcaccgc ttatacggta tcgcgatcaa tatgaatcgc   1080
gtctttaaag tcaataccaa cgcgtactac gaaatgaccg gcttagaggt tagctttgaa   1140
gaattacgca ccttcggtgg ccacgacgcc aagttcatcg acagcctgca ggaaaatgag   1200
ttccgcttgt actattacaa taaattcaag gacatcgcga gcaccttaaa taaagcaaag   1260
agcattgtgg gcaccaccgc aagcttgcag tacatgaaga acgtatttaa ggaaaaatat   1320
ttgttgtcgg aggataccag cgggaaattc agcgtcgata agctgaaaatt cgacaaattg   1380
tataaaatgc tgaccgagat ttacaccgag gataacttcg tcaagttttt taaggtgtta   1440
aatcgtaaga cctatttaaa cttgataaa gcggtgttta aaattaatat cgtgccgaag   1500
gtgaattaca ccatctacga tggtttcaac ttaagcaaca cgaatctggc ggcgaatttt   1560
aatggccaaa acaccgaaat taacaacatg aactttacga agttaaagaa tttcacgggc   1620
ttattcgaat tctacaagtt attatgcgtg cgcggcatca ttaccagcaa ggcaggtgcg   1680
ggcaagtcct tggttccgcg tggcagcgcc ggcgccggcg cgctcaatga tctgtgtatt   1740
aaagtcaata actgggaccct gttcttcagc ccgagcgagg ataactttac caacgactta   1800
aacaaaggcg aggagatcac gagcgatacg aacatcgagg cggcggagga aatatattagc   1860
ctggacctca ttcagcagta ctatctgacg ttcaattttg acaatgagcc ggagaacatc   1920
agcattgaaa atctcagcag cgacatcatc ggtcagttgg aactgatgcc gaacattgaa   1980
cgctttccga acggcaaaaa atatgaactg gacaagtata ccatgttcca ttacttacgc   2040
gcacaggaat ttgagcacgg caagagccgc attgcgctga ccaatagcgt taacgaggcc   2100
ttgttaaatc cgagccgtgt ctacacgttc ttcagcagcg attatgtcaa aaaagtgaac   2160
aaggcgaccg aagccgcgat gttttttggc tgggtcgagc aattggttta cgattttacc   2220
gacgaaacca gcgaggtgag cacgaccgac aaaattgcag atatcaccat catcattccg   2280
tacatcggtc cggcgctcaa tatcggcaat atgttataca aggacgactt tgtgggcgcg   2340
ctgatctta gcggcgcggt tatcttatta gaattcatcc cggagatcgc aatcccggtc   2400
ttgggcaccct ttgcgttggt gagctatatc gcgaataaag tgctcacggt ccaaaccatc   2460
gataacgcgc tcagcaagcg taatgagaaa tgggacgagg tttataagta tatcgtgacc   2520
aactggttag caaagtcaa tacgcagatc gatctcatcc gcaaaaaaat gaagaagcc   2580
ttggaaaatc aagcggaggc aaccaaagcc atcattaatt accagtataa ccaatatacc   2640
gaagaagaaa aaacaatat caacttcaat atcgatgatt tgagcagcaa actgaacgag   2700
```

```
agcattaaca aagcgatgat taacatcaac aagttcttga atcaatgcag cgtgagctat    2760
ctcatgaaca gcatgatccc gtatggcgtc aaacgcttgg aagattttga cgccagcctg    2820
aaagatgcgc tcctcaagta tatttatgac aaccgcggca ccctcattgg ccaggtggac    2880
cgcttgaagg ataaagtgaa caatacgctc agcacggata tcccgttcca gctgagcaag    2940
tacgtcgaca accagcgctt actgagcacc tttaccgagt atatcaagaa catcattaat    3000
accagcatcc tcaacttgcg ctatgagagc aatcacctga tcgacctcag ccgctacgcc    3060
agcaagatca acatcggcag caaggtcaat ttcgacccga tcgataagaa tcagatccaa    3120
ttgtttaacc tggaaagcag caagatcgag gttatcttga agaacgcgat tgtgtacaac    3180
agcatgtacg agaactttag cacgagcttc tggattcgta tcccgaagta tttcaatagc    3240
attagcctga ataacgaata taccattatc aactgcatgg aaaataatag cggctggaag    3300
gtgagcttaa attcggcga gatcatttgg accttacagg atacccaaga aatcaaacag    3360
cgcgtcgtct ttaagtatag ccagatgatc aacatcagcg attacatcaa ccgctggatc    3420
ttcgtgacca tcaccaataa tcgcttgaat aatagcaaga tttacatcaa tggtcgcttg    3480
attgatcaaa aaccgatcag caatctcggt aatatccatg ccagcaataa catcatgttt    3540
aagttagacg gttgccgcga tacccaccgc tatatctgga tcaagtattt taacttattt    3600
gataaggaac tcaacgaaaa ggaaattaaa gacttatatg acaatcagag caatagcggc    3660
atcctgaagg atttctgggg cgactacctg cagtacgata gccgtacta tatgttgaac    3720
ttgtatgacc cgaacaaata tgtcgatgtg aacaatgtgg gtattcgtgg ctatatgtac    3780
ttaaagggcc cgcgtggtag cgtgatgacc acgaatattt acttaaacag cagcttatac    3840
cgcggcacga agtttattat caagaagtat gccagcggca acaaggacaa tatcgtccgc    3900
aacaacgacc gtgtgtatat taacgtggtg gtgaagaata aagagtaccg cttggccacg    3960
aatgcgagcc aggcgggcgt ggaaaaaatc ttgagcgcgt tggagatccc ggacgtcggc    4020
aacctcagcc aggttgtggt gatgaagtct aaaaacgacc agggcatcac gaacaagtgc    4080
aaaatgaatt tgcaagataa caacggcaac gacatcggct ttattggttt tcaccagttc    4140
aataacatcg ccaaactcgt ggccagcaat tggtataacc gccaaattga acgcagcagc    4200
cgcacgctcg gctgtagctg ggagttcatc ccggtggacg atggctgggg cgagcgcccg    4260
ctcgcaagtc cggcagcacc ggcaccggct tcaccagctg caccagcacc tagcgcaccg    4320
gcagcatctc cagcagcccc tgcaccggca agccctgcag ctccagcacc gtcagcacca    4380
gcagcaagcc cagctgctcc tgctccagcg agcccagcag cgccagctcc tagtgccct    4440
gctgcctctc ctgctgctcc ggcaccagca agtcctgctg cgcctgcacc gagtgctccg    4500
gctgctagtc ctgccgcacc agctccggct agtccagctg ctccagcccc ttcagcccct    4560
gcaggagatc tggtgccacg cggttccgcg aattcgagct ccgtcgacaa gctttggagc    4620
cacccgcagt tcgaaaaata a                                              4641
```